(12) United States Patent
Bachelder et al.

(10) Patent No.: US 11,110,001 B2
(45) Date of Patent: *Sep. 7, 2021

(54) EXPANDABLE DRUG DELIVERY DEVICES AND METHODS OF USE

(71) Applicant: ForSight Vision4, Inc., South San Francisco, CA (US)

(72) Inventors: Bradley G. Bachelder, South San Francisco, CA (US); Randolph E. Campbell, South San Francisco, CA (US); Darren G. Doud, South San Francisco, CA (US); Signe R. Erickson, South San Francisco, CA (US); Kevin W. Sacherman, South San Francisco, CA (US)

(73) Assignee: ForSight Vision4, Inc., South San Francisco, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 16/671,749

(22) Filed: Nov. 1, 2019

(65) Prior Publication Data

US 2020/0060874 A1 Feb. 27, 2020

Related U.S. Application Data

(63) Continuation of application No. 14/937,754, filed on Nov. 10, 2015, now Pat. No. 10,500,091.

(Continued)

(51) Int. Cl.
*A61F 9/00* (2006.01)
*A61K 9/00* (2006.01)

(52) U.S. Cl.
CPC .......... *A61F 9/0017* (2013.01); *A61K 9/0051* (2013.01); *A61F 2210/0014* (2013.01);
(Continued)

(58) Field of Classification Search
CPC ............ A61F 9/0017; A61F 2250/0069; A61F 2250/0068; A61F 2250/001;
(Continued)

(56) References Cited

U.S. PATENT DOCUMENTS 2,564,977 A 8/1951 Hu et al.
2,585,815 A 2/1952 McLintock
(Continued)

FOREIGN PATENT DOCUMENTS

CN 1538826 A 10/2004
CN 101052435 A 10/2007
(Continued)

OTHER PUBLICATIONS

U.S. Appl. No. 13/814,466, filed Jun. 28, 2013, 2013/0274691.
(Continued)

*Primary Examiner* — Jenna Zhang
(74) *Attorney, Agent, or Firm* — Mintz Levin Cohn Ferris Glovsky and Popeo, P.C.

(57) ABSTRACT

Described are implantable devices having expandable reservoirs for the sustained release of therapeutic agents. The device is configured to be at least partially implanted in an eye and includes a retention structure and a penetrable element coupled to and extending within at least a portion of the retention structure. A porous drug release mechanism is positioned in fluid communication with an outlet of the device; and a reservoir having a volume configured to contain one or more therapeutic agents is in fluid communication with the outlet through the porous drug release mechanism. The device is at least partially inserted along an axis of insertion. The reservoir enlarges from an insertion configuration having a first three-dimensional shape to an expanded configuration having a second three-dimensional (Continued)

shape, the second three-dimensional shape being eccentrically positioned relative to the axis of insertion.

22 Claims, 26 Drawing Sheets

Related U.S. Application Data

(60) Provisional application No. 62/077,829, filed on Nov. 10, 2014.

(52) U.S. Cl.
CPC .......... *A61F 2210/0061* (2013.01); *A61F 2250/001* (2013.01); *A61F 2250/0068* (2013.01); *A61F 2250/0069* (2013.01)

(58) Field of Classification Search
CPC ..... A61F 2210/0061; A61F 2210/0014; A61K 9/0051
See application file for complete search history.

(56) References Cited

U.S. PATENT DOCUMENTS

| | | |
|---|---|---|
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shell |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,213,576 A | 5/1993 | Abiuso et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,554,132 A | 9/1996 | Straits et al. |
| 5,562,915 A | 10/1996 | Lowe et al. |
| 5,578,042 A | 11/1996 | Cumming |
| 5,681,572 A | 10/1997 | Seare, Jr. |
| 5,702,414 A | 12/1997 | Richter et al. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,904,144 A | 5/1999 | Hammang et al. |
| 5,916,584 A | 6/1999 | O'Donoghue et al. |
| 5,928,662 A | 7/1999 | Phillips |
| 5,951,512 A | 9/1999 | Dalton |
| 5,972,369 A | 10/1999 | Roorda et al. |
| 5,985,328 A | 11/1999 | Chu et al. |
| 5,993,414 A | 11/1999 | Haller |
| 6,001,386 A | 12/1999 | Ashton et al. |
| 6,123,861 A | 9/2000 | Santini, Jr. et al. |
| 6,183,461 B1 | 2/2001 | Matsuura et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,306,426 B1 | 10/2001 | Olejnik et al. |
| 6,331,313 B1 | 12/2001 | Wong et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |

(56) References Cited

U.S. PATENT DOCUMENTS

| | | |
|---|---|---|
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,009,039 B2 | 3/2006 | Yayon et al. |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,083,803 B2 | 8/2006 | Peyman |
| 7,087,237 B2 | 8/2006 | Peyman |
| 7,090,681 B2 | 8/2006 | Weber et al. |
| 7,094,226 B2 | 8/2006 | Yaacobi |
| 7,117,870 B2 | 10/2006 | Prescott |
| 7,141,023 B2 | 11/2006 | Diermann et al. |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,384,648 B2 | 6/2008 | Olejnik et al. |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 7,998,497 B2 | 8/2011 | de Juan, Jr. et al. |
| 8,034,369 B2 | 10/2011 | Anderson et al. |
| 8,038,650 B2 | 10/2011 | Shekalim |
| 8,096,972 B2 | 1/2012 | Varner et al. |
| 8,231,608 B2 | 7/2012 | Pang et al. |
| 8,231,609 B2 | 7/2012 | Pang et al. |
| 8,277,830 B2 | 10/2012 | de Juan, Jr. et al. |
| 8,308,755 B2 | 11/2012 | Cronin et al. |
| 8,348,877 B2 | 1/2013 | Tu et al. |
| 8,348,897 B2 | 1/2013 | Shih et al. |
| 8,399,006 B2 | 3/2013 | de Juan, Jr. et al. |
| 8,486,052 B2 | 7/2013 | Varner et al. |
| 8,623,395 B2 | 1/2014 | de Juan, Jr. et al. |
| 8,795,711 B2 | 8/2014 | de Juan, Jr. et al. |
| 8,821,474 B2 | 9/2014 | Shekalim |
| 8,864,703 B2 | 10/2014 | LaBelle |
| 8,992,503 B2 | 3/2015 | Shekalim |
| 9,033,911 B2 | 5/2015 | de Juan, Jr. et al. |
| 9,084,662 B2 | 7/2015 | Gifford, III et al. |
| 9,883,968 B2 | 2/2018 | Doud et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0209359 A1 | 10/2004 | Yayon et al. |
| 2004/0230183 A1 | 11/2004 | Breegi et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0020253 A1* | 1/2006 | Prescott ............ A61F 9/00772 604/500 |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212397 A1 | 9/2007 | Roth |
| 2007/0233037 A1 | 10/2007 | Gifford et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |

(56) References Cited

U.S. PATENT DOCUMENTS

| | | |
|---|---|---|
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0286338 A1 | 11/2008 | Rosenthal et al. |
| 2008/0292679 A1 | 11/2008 | Lyons et al. |
| 2008/0293691 A1 | 11/2008 | Brigandi et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0192493 A1 | 7/2009 | Meng et al. |
| 2009/0214601 A1 | 8/2009 | Chappa et al. |
| 2009/0224064 A1 | 9/2009 | Brodbeck et al. |
| 2009/0234449 A1 | 9/2009 | De Juan, Jr. et al. |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1* | 5/2010 | Lenker ............ A61B 17/12186 604/96.01 |
| 2010/0114309 A1 | 5/2010 | de Juan, Jr. et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0223979 A1 | 9/2010 | Ploehn et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1* | 11/2010 | Goldsmith ......... A61B 17/0057 623/23.7 |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0206646 A1 | 8/2011 | Alfonso et al. |
| 2011/0208122 A1 | 8/2011 | Shekalim |
| 2012/0028918 A1 | 2/2012 | Gupta |
| 2012/0029445 A1 | 2/2012 | de Juan, Jr. et al. |
| 2012/0029470 A1 | 2/2012 | Juan, Jr. et al. |
| 2012/0095439 A1* | 4/2012 | de Juan, Jr. ............ A61K 45/06 604/506 |
| 2012/0183799 A1 | 7/2012 | Steele et al. |
| 2012/0184905 A1 | 7/2012 | Shekalim |
| 2012/0209077 A1 | 8/2012 | Racenet |
| 2013/0116664 A1 | 5/2013 | Tai et al. |
| 2013/0165860 A1 | 6/2013 | Doud et al. |
| 2013/0204209 A1 | 8/2013 | de Juan, Jr. et al. |
| 2013/0218081 A1 | 8/2013 | Roth |
| 2013/0245544 A1 | 9/2013 | de Juan, Jr. et al. |
| 2013/0245573 A1 | 9/2013 | de Juan, Jr. et al. |
| 2013/0274691 A1 | 10/2013 | de Juan, Jr. et al. |
| 2013/0274692 A1 | 10/2013 | Alster et al. |
| 2013/0289482 A1 | 10/2013 | Meng et al. |
| 2013/0289497 A1 | 10/2013 | Humayun et al. |
| 2013/0296810 A1 | 11/2013 | Humayun et al. |
| 2013/0304031 A1 | 11/2013 | Varner et al. |
| 2013/0324918 A1 | 12/2013 | de Juan, Jr. et al. |
| 2013/0324942 A1 | 12/2013 | de Juan, Jr. et al. |
| 2014/0031769 A1 | 1/2014 | de Juan, Jr. et al. |
| 2014/0031833 A1 | 1/2014 | Novakovic et al. |
| 2014/0033800 A1 | 2/2014 | Farinas et al. |
| 2014/0073714 A1 | 3/2014 | Reich et al. |
| 2014/0121609 A1 | 5/2014 | de Juan, Jr. et al. |
| 2014/0221941 A1 | 8/2014 | Erickson et al. |
| 2014/0243795 A1 | 8/2014 | Varner et al. |
| 2014/0276482 A1 | 9/2014 | Astafieva et al. |
| 2014/0296800 A1 | 10/2014 | Erickson et al. |
| 2014/0328894 A1 | 11/2014 | de Juan, Jr. et al. |
| 2014/0336619 A1 | 11/2014 | Stankus et al. |
| 2014/0358125 A1 | 12/2014 | de Juan, Jr. et al. |
| 2015/0080846 A1 | 3/2015 | de Juan, Jr. et al. |

(56) References Cited

U.S. PATENT DOCUMENTS

| | | | |
|---|---|---|---|
| 2015/0133896 A1 | 5/2015 | Benner et al. |
| 2015/0202079 A1 | 7/2015 | Shekalim |
| 2015/0224200 A1 | 8/2015 | de Juan, Jr. et al. |
| 2015/0231265 A1 | 8/2015 | Gupta |
| 2015/0250647 A1 | 9/2015 | de Juan, Jr. et al. |
| 2015/0282983 A1 | 10/2015 | Benner et al. |
| 2015/0297402 A1 | 10/2015 | de Juan, Jr. et al. |
| 2015/0351796 A1 | 12/2015 | Richard et al. |
| 2016/0038488 A1 | 2/2016 | Horvath et al. |
| 2016/0101046 A1 | 4/2016 | Reich et al. |
| 2016/0128867 A1 | 5/2016 | Bachelder et al. |
| 2016/0184134 A1 | 6/2016 | Varner et al. |
| 2016/0258855 A1 | 9/2016 | Farinas et al. |
| 2016/0270955 A1* | 9/2016 | Shekalim .......... A61M 5/14276 |
| 2016/0302965 A1 | 10/2016 | Erickson et al. |
| 2017/0165108 A1 | 6/2017 | Bianchi et al. |
| 2017/0165110 A1 | 6/2017 | Erickson et al. |
| 2017/0172794 A1 | 6/2017 | Varner et al. |
| 2017/0258634 A1 | 9/2017 | de Juan, Jr. et al. |
| 2018/0147204 A1 | 5/2018 | Horvath et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |
| 2018/0289542 A1 | 10/2018 | de Juan, Jr. et al. |
| 2018/0292403 A1 | 10/2018 | de Juan, Jr. et al. |
| 2019/0336335 A1 | 11/2019 | de Juan, Jr. et al. |
| 2019/0350754 A1 | 11/2019 | Bianchi et al. |
| 2019/0365757 A1 | 12/2019 | Horvath et al. |
| 2020/0030142 A1 | 1/2020 | Erickson et al. |

FOREIGN PATENT DOCUMENTS

| | | |
|---|---|---|
| CN | 1019698970 A | 2/2011 |
| CN | 102596097 A | 7/2012 |
| EP | 0 228 185 A1 | 11/1986 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 | 6/2006 |
| EP | 1385452 B1 | 9/2006 |
| EP | 1409065 B1 | 1/2007 |
| EP | 1337284 B1 | 12/2007 |
| EP | 1911481 | 4/2008 |
| EP | 1521572 B1 | 3/2009 |
| JP | 01-149716 A | 6/1989 |
| JP | 01-197429 A | 8/1989 |
| RU | 2414199 C2 | 3/2011 |
| WO | WO-88/04573 | 6/1988 |
| WO | WO-90/07545 | 7/1990 |
| WO | WO-95/28984 A1 | 11/1995 |
| WO | WO-97/29850 | 8/1997 |
| WO | WO-98/25982 | 6/1998 |
| WO | WO-99/11244 | 3/1999 |
| WO | WO-00/48660 | 8/2000 |
| WO | WO-01/26714 | 4/2001 |
| WO | WO-01/50943 | 7/2001 |
| WO | WO-0168016 | 9/2001 |
| WO | WO-02/100318 | 12/2002 |
| WO | WO-03/077972 | 9/2003 |
| WO | WO-03/082188 | 10/2003 |
| WO | WO-2004/000267 | 12/2003 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/050221 | 5/2006 |
| WO | WO-2006/068838 | 6/2006 |
| WO | WO-2006/071554 | 7/2006 |
| WO | WO-2006/082588 | 8/2006 |
| WO | WO-2006/108054 | 10/2006 |
| WO | WO-2006/127962 | 11/2006 |
| WO | WO-2006/138609 | 12/2006 |
| WO | WO-2007/012974 | 2/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO 2007//066339 | 6/2007 |
| WO | WO 2007//084582 | 7/2007 |
| WO | WO-2007/084765 | 7/2007 |
| WO | WO-2007/101204 | 9/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 A2 | 5/2008 |
| WO | WO-2008/076544 | 6/2008 |
| WO | WO-2008/094989 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |
| WO | WO-2009/055671 | 4/2009 |
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010/075565 | 7/2010 |
| WO | WO-2010/078063 | 7/2010 |
| WO | WO-2010/088548 | 8/2010 |
| WO | WO-2010/093945 | 8/2010 |
| WO | WO-2010/095940 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/079232 | 6/2011 |
| WO | WO-2012/019047 A2 | 2/2012 |
| WO | WO-2012/019136 | 2/2012 |

(56) References Cited

FOREIGN PATENT DOCUMENTS

| WO | WO-2012/065006 A2 | 5/2012 |
|---|---|---|
| WO | WO-2014/160884 A1 | 10/2014 |
| WO | WO-2015/059680 A1 | 4/2015 |

OTHER PUBLICATIONS

U.S. Appl. No. 14/753,574, filed Jun. 29, 2015, 2015/0297402.
U.S. Appl. No. 15/102,191, filed Jun. 6, 2016, 2016/0302965.
U.S. Appl. No. 15/606,647, filed May 26, 2017, 2017/0258634.
U.S. Appl. No. 15/807,396, filed Nov. 8, 2017, 2018/0292403.
U.S. Appl. No. 15/877,146, filed Jan. 22, 2018, 2018/0243130.
U.S. Appl. No. 16/004,085, filed Jun. 8, 2018, 2018/0289542.
U.S. Appl. No. 16/091,493, filed Oct. 4, 2018, 2019/0117454.
U.S. Appl. No. 16/380,786, filed Apr. 10, 2019, 2019/0350754.
U.S. Appl. No. 16/386,854, filed Apr. 17, 2019, 2019/0336335.
U.S. Appl. No. 16/434,966, filed Jun. 7, 2019, 2019/0365757.
U.S. Appl. No. 16/540,617, filed Aug. 14, 2019, 2020/0030142.
PCT/US2018/61262, Nov. 15, 2018, WO 2019/10396.
Andrews, "Effect of nonsteroidal anti-inflammatory drugs on LFA-1 and ICAM-1 expression in gastric mucosa," Am J Physiol. Apr. 1994. 266(4 Pt 1):G657-664.
Avery et al., "Intravitreal bevacizumab (Avastin) in the treatment of proliferative diabetic retinopathy," Ophthalmology. Oct. 2006, 113(10):1695-1705.e6.
Bakri et al., "The effect of intravitreal triamcinolone acetonide on intraocular pressure," Ophthalmic Surgery, Lasers and Imaging, Sep./Oct. 2003; 34(5): 386-390.
Bird et al., Transport Phenomena, John Wiley & Sons, Inc., New York, 1960, pp. 196-201.
Block et al., "Solubility and dissolution of triamcinolone acetonide," Journal of Pharmaceutical Sciences, Apr. 1973; 62(4):617-621.
Castro et al., "Effect of COX inhibitors on VEGF-induced retinal vascular leakage and experimental corneal and choroidal neovascularization," Exp Eye Res. Aug. 2004; 79(2):275-285.
Chirila et al., "The Vitreous Humor" in *Handbook of Biomaterial Properties*, eds. Black & Hastings. Chapman & Hall, London, 1998; pp. 125-131.
Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.
Deissler et al., "VEGF-induced effects on proliferation, migration and tight junctions are restored by ranibizumab (Lucentis) in microvascular retinal endothelial cells," Br J Ophthalmol 2008;92:839-843.
Donoso et al., "The role of inflammation in the pathogenesis of age-related macular degeneration," Surv Ophthalmol. Mar.-Apr. 2006;51(2):137-52.
European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.
Funatsu et al. "Association of vitreous inflammatory factors with diabetic macular edema," Ophthalmology 2009;116:73-79.
Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.
Gillies et al., "Intravitreal triamcinolone for refractory diabetic macular edema: two-year results of a double-masked, placebo-controlled, randomized clinical trial," Ophthalmology. Sep. 2006;113(9):1533-1538.
Hastedt & Wright, "Diffusion in porous materials above the percolation threshold," Pharm. Res. Sep. 1990; 7(9):893-901 (1990).
Heier et al, "Ketorolac versus prednisolone versus combination therapy in the treatment of acute pseudophakic cystoid macular edema," Ophthalmology. Nov. 2000;107(11):2034-2038 ;discussion 2039.
Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.
Kang et al., "Inhibitory effects of anti-inflammatory drugs on interleukin-6 bioactivity," Biol Pharm Bull. Jun. 2001;24(6):701-703.
Lopez-Armada et al., "Modulation of cell recruitment by anti-inflammatory agents in antigen-induced arthritis," Ann Rheum Dis Nov. 2002;61(11):1027-1030.
Luncentis, INN-Ranibizumab, "Scientific Discussion," European Medicines Agency ; retrieved from the Internet:<http://www.ema.europa.eu/docs/en_GB/document_library/EPAR_-_Assessment_Report_-_Variation/human/000715/WC500101009.pdf>. Oct. 21, 2010. 32 pages.
Metal Powder Industries Federation, Porous Metal Design Guidebook, 2007, 24 pages total. Downloaded from the Internet: <<http://www.mpif.org/DesignCenter/porous.pdf>>.
MOTT Corporation, "Sintered Metal Powder Media," American Filtration & Separation Society 2007, 2 pages total. Downloaded from the Internet:<<http://www.afssociety.org/education/0907oneminute.htm>>.
Navarro, "The Optical Design of the Human Eye: a Critical Review," J Optom, Jan.-Mar. 2009 2(1): 3-18.
Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.
Rosenfeld, "The Latest Research: Intravitreal Bevacizumab for Proliferative Diabetic Retinopathy," Review of Ophthalmology's Retina Online, Feb. 2006. 2 pages. Retrieved from the Internet: http://www.revophth.com/archive/newsletter/0206_retina.htm.
Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).
Smith et al., "Spectrophotometric determination of pKa values for fluorescein using activity coefficient corrections," WaterSA 2002; 28(4):395-402.
Smith, T.J., et al., "Intravitreal Sustained-Release Ganciclovir", *Arch. Ophthamol* 110 (1992) pp. 255-258.
Soheilian et al., "Pilot Study of Intravitreal Injection of Diclofenac for Treatment of Macular Edema of Various Etiologies," Retina, Mar. 2010; 30(3): 509-515.
Theodossiadis et al., "Intravitreal administration of the anti-tumor necrosis factor agent infliximab for neovascular age-related macular degeneration," Am J Ophthalmol. May 2009;147(5):825-830.
Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.

* cited by examiner

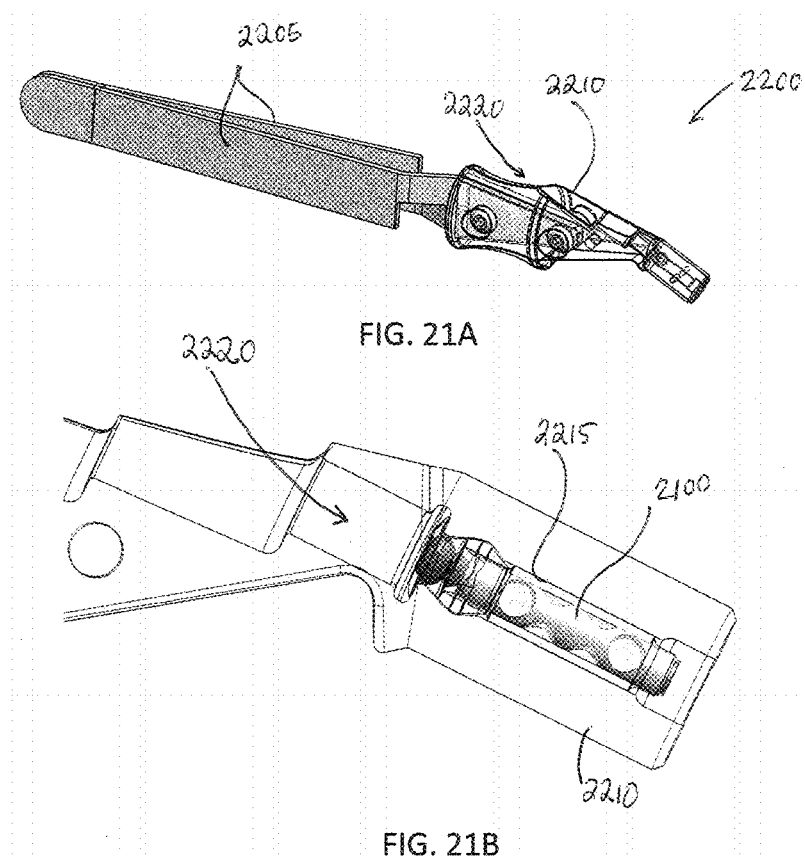

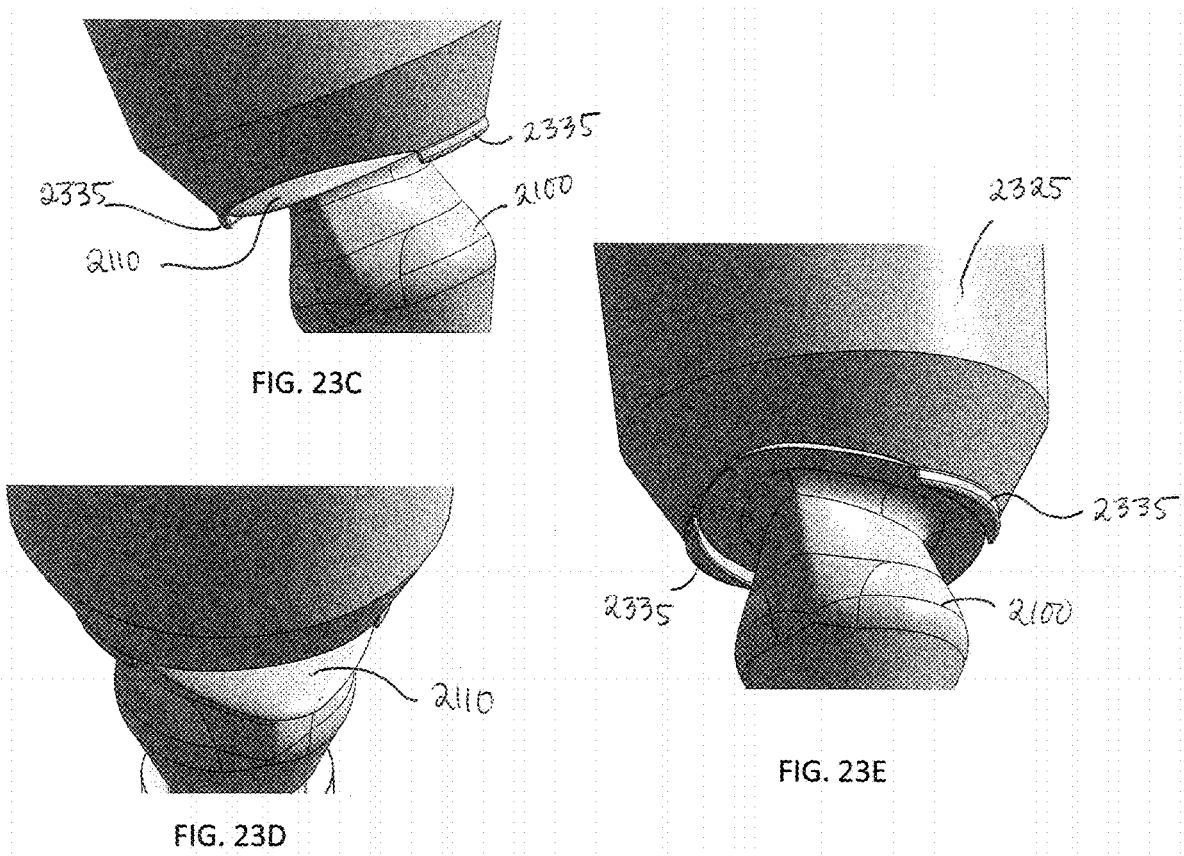

EXPANDABLE DRUG DELIVERY DEVICES AND METHODS OF USE

CROSS-REFERENCE TO PRIORITY DOCUMENT

This application is a continuation of U.S. application Ser. No. 14/937,754, filed Nov. 10, 2015, now U.S. Pat. No. 10,500,091, which claims the benefit of priority of U.S. Provisional Patent Application Ser. No. 62/077,829, entitled "Expandable Drug Delivery Devices and Methods of Use," filed Nov. 10, 2014. Priority of the filing date is hereby claimed and the full disclosures are hereby incorporated by reference.

BACKGROUND

Diseases that affect vision can be treated with a variety of therapeutic agents, but the delivery of drugs to the eye continues to be challenging. Injections of therapeutic via the eye can be painful, involve some risk of infection, hemorrhage and retinal detachment. Depending on the frequency, intra-ocular injections can be time-consuming for both patient and physician. Consequently, in at least some instances the drug may be administered less often than the prescribed frequency resulting in sub-optimal treatment benefit. Further, bolus intra-ocular injections may not provide the ideal pharmacokinetics and pharmacodynamics. A bolus injection of drug into the vitreous humor of a patient can result in a peak drug concentration several times higher than the desired therapeutic amount and then before the patient is able to get the next injection drop to a drug concentration that is far below therapeutic effectiveness.

SUMMARY

In one aspect, disclosed is a drug delivery device configured to be at least partially implanted in an eye. The device includes a retention structure positioned near a proximal end region of the device; a penetrable element coupled to and extending within at least a portion of the retention structure; a porous drug release mechanism positioned in fluid communication with an outlet of the device; and a reservoir having a volume configured to contain one or more therapeutic agents and to be in fluid communication with the outlet through the porous drug release mechanism. The device is configured to be at least partially inserted into the eye along an axis of insertion. The reservoir is configured to enlarge from an insertion configuration having a first three-dimensional shape to an expanded configuration having a second three-dimensional shape. The second three-dimensional shape is eccentrically positioned relative to the axis of insertion.

A portion of the volume of the reservoir in the expanded configuration can enlarge away from the lens of the eye and can be greater than a remaining portion of the volume. The first portion and the remaining portion can each remain outside the visual axis of the eye. The reservoir can be formed of a non-compliant material. The non-compliant material of the reservoir can expand from the first three-dimensional shape to the second three-dimensional shape, but does not stretch beyond the second three-dimensional shape. A proximal end of the reservoir can be separated a distance from one or more internal tissue surfaces surrounding penetration site of the eye when in the expanded configuration. The device can remain outside the visual axis in the expanded configuration.

The device can further include a central core element extending from the proximal end region of the device to a distal end region of the device. The drug release mechanism can be coupled to the central core element near the distal end region of the device and the retention structure can be coupled to the central core element near the proximal end region of the device. The central core element can include an inner lumen and one or more openings extending through a wall of the central core element. The inner lumen of the central core element can be in fluid communication with the reservoir volume through the one or more openings. The one or more openings can direct flow of material injected into the device into the reservoir volume. The central core element can have a cylindrical geometry and further include a flow director to direct flow through the one more openings. The flow director can include a first cylindrical region coupled to a second cylindrical region by a funnel shaped region. The first cylindrical region can have a larger cross-sectional diameter than the second cylindrical region. The flow director can include a penetrable barrier positioned within the inner lumen of the central core element. The penetrable barrier can seal the inner lumen.

The retention structure can include a proximal flange element configured to extend outside a sclera of the eye and a neck. The neck can have a proximal region configured to extend through a penetration site in the sclera of the eye and a distal extension extending inside the sclera of the eye. The distal extension of the neck can surround a portion of the central core element near the proximal end of the device providing stabilization of the neck to maintain a position of the reservoir. The distal extension of the neck can prevent contact between the reservoir and internal surfaces of the eye adjacent the penetration site. An upper surface of the proximal flange element can indicate orientation of the reservoir in the expanded configuration. The upper surface of the flange element can include an orientation indicator visible to a user from outside the eye. The orientation indicator can be a shape of the flange element or a mark on the upper surface of the flange element. The distal extension of the neck can provide stabilization of the neck to maintain a position of the reservoir as indicated by the orientation indicator.

In an interrelated implementation, described is a drug delivery device that includes a proximal end region of the device having a retention structure and a penetrable element coupled to and extending within at least a portion of the retention structure; and a distal end region of the device configured to be at least partially implanted into an eye. The distal end region can include a porous drug release mechanism positioned in fluid communication with an outlet of the device; and a reservoir having a volume configured to contain one or more therapeutic agents and to be in fluid communication with the outlet through the porous drug release mechanism. The reservoir is configured to enlarge from an insertion configuration to an expanded configuration. After at least partial implantation in the eye along an axis of insertion, the device is configured to be changed from a first shape in which the distal end region of the device is aligned with the axis of insertion to a second shape in which the distal end region of the device is not aligned with the axis of insertion. The second shape can be a curvilinear shape that remains outside the visual axis of the eye and avoids contact with internal surfaces of the eye adjacent a penetration site. The expanded configuration of the reservoir can include a symmetrical expansion. The expanded configuration of the reservoir can be an asymmetrical expansion.

In an interrelated implementation, described is a drug delivery device configured to be at least partially implanted in an eye that includes a reservoir formed of non-compliant material forming a volume configured to contain one or more therapeutic agents. The device includes a central core element extending through the volume between a proximal end region of the reservoir and a distal end region of the reservoir. The central core element has a wall surrounding a lumen, an inlet to the lumen, an outlet from the lumen, and one or more openings extending through the wall of the central core element between the inlet and the outlet. The lumen is in fluid communication with the volume of the reservoir via the one or more openings. The device includes a porous drug release mechanism positioned within the outlet and configured to release the one or more therapeutic agents from the volume through the porous drug release mechanism. The non-compliant material of the reservoir is collapsed around the central core element forming a first three-dimensional shape prior to filling the volume with the one or more therapeutic agents when the device is in an insertion configuration. The non-compliant material of the reservoir is enlarged away from the central core element forming a second three-dimensional shape upon filling the volume with the one or more therapeutic agents when the device is in an expanded configuration.

The device can further include a retention structure positioned near a proximal end region of the device and a penetrable element coupled to and extending within at least a portion of the retention structure. The device can further include a flow director positioned within the lumen of the central core element. The flow director can be configured to facilitate filling of the reservoir volume. The flow director can include a first cylindrical region coupled to a second cylindrical region by a funnel-shaped region to direct flow through the one or more openings in the central core element. The first cylindrical region can have a larger cross-sectional diameter than the second cylindrical region.

In some variations, one or more of the following can optionally be included in any feasible combination in the above methods, apparatus, devices, and systems. More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIG. 21A is a priming tool for use with a treatment device;

FIG. 21B is a close-up view of the distal end of the priming tool in FIG. 21A and having a treatment device in an unexpanded configuration held therein;

FIGS. 23C-23E are detailed views of the distal end region of the insertion tool of FIGS. 23A-23B coupled with a proximal end of a treatment device;

DETAILED DESCRIPTION

Figure 1:
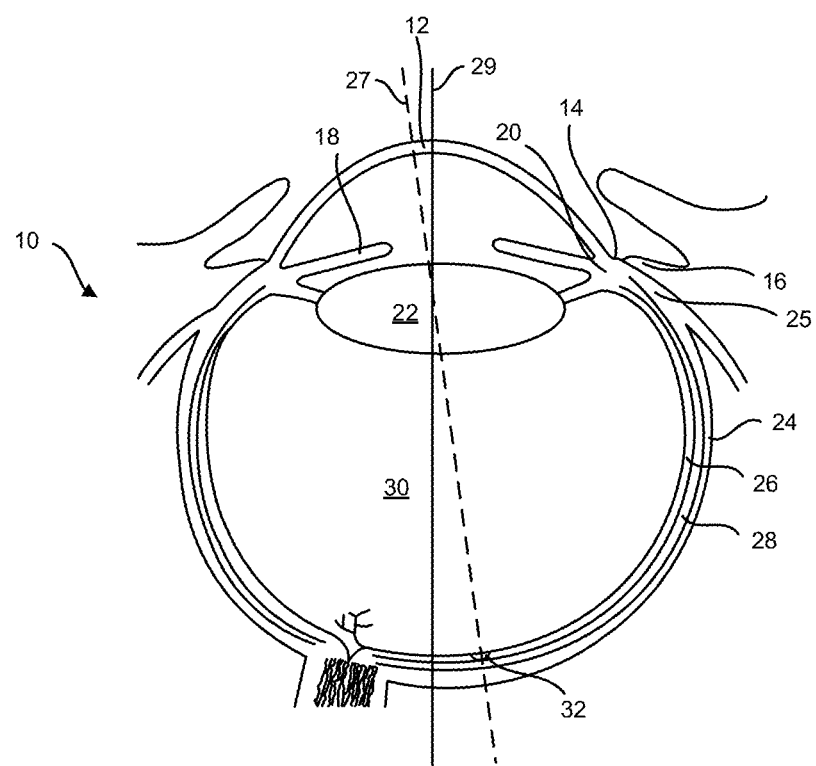
FIG. 1 is a cross-sectional, schematic view of a portion of the human eye.

Described herein are implantable devices, systems and methods of use for the delivery of one or more therapeutics for the treatment of diseases. The devices and systems described herein maximize reservoir volume and capacity while minimizing overall device invasiveness and impact on eye anatomy and vision. In some implementations, the devices described herein include an expandable reservoir that can be compressed into a first configuration for minimally-invasive delivery into the eye, for example, through the sclera and expanded into a second, enlarged configuration upon filling with therapeutic agent following implantation in the eye. When in the second configuration, the reservoir can avoid interfering with the visual axis of the eye as well as remain a safe distance away from certain anatomical structures of the eye so as to avoid damage and impacting vision. As will be described herein, in some implementations the expandable reservoir in the expanded configuration takes on a shape that is eccentric, asymmetrical, or otherwise off-set from the axis of placement of the device into the eye tissue, for example an axis of insertion through the sclera. This off-set can result in a majority of the expanded volume of the reservoir being directed away from certain critical structures of the anterior segment of the eye, for example, the lens, the ciliary body, the choroid, the retina, as well as the sclera and surrounding internal tissue layers through which the device was inserted. In other implementations, the expandable reservoir in the expanded configuration can remain symmetrical or coaxial with a central axis of the device, but can be shaped such that at least a portion of the device is curved, angled, or otherwise off-set relative to the axis of insertion. For example, the expanded reservoir can be shaped into an arc or other curvilinear shape relative to the axis of insertion. Alternatively, the expanded reservoir can be shaped to form an angle relative to the axis of insertion. In these implementations, the overall length of the device can be increased while still remaining outside the visual axis or significantly impacting the visual field. These and other features of the devices described herein will be described in more detail below.

It should be appreciated that the devices and systems described herein can incorporate any of a variety of features described herein and that elements or features of one implementation of a device and system described herein can be incorporated alternatively or in combination with elements or features of another implementation of a device and system described herein as well as the various implants and features described in U.S. Pat. Nos. 8,399,006; 8,623,395; PCT Pat. Publication No. WO2012/019136; PCT Pat. Publication No. WO2012/019047; and PCT Pat. Publication No. WO 2012/065006; the entire disclosures of which are incorporated herein by reference thereto. For example, the expandable reservoirs described herein may be used with any of the various implementations of a device or system. For the sake of brevity, explicit descriptions of each of those combinations may be omitted although the various combinations are to be considered herein. Additionally, described herein are different methods for implantation and access of the devices. The various implants can be implanted, filled, refilled etc. according to a variety of different methods and using a variety of different devices and systems. Provided are some representative descriptions of how the various devices may be implanted and accessed, however, for the sake of brevity explicit descriptions of each method with respect to each implant or system may be omitted.

It should also be appreciated that the devices and systems described herein can be positioned in many locations of the eye and need not be implanted specifically as shown in the figures or as described herein. The devices and systems described herein can be used to deliver therapeutic agent(s) for an extended period of time to one or more of the following tissues: intraocular, intravascular, intraarticular, intrathecal, pericardial, intraluminal and intraperitoneal. Although specific reference is made below to the delivery of treatments to the eye, it also should be appreciated that medical conditions besides ocular conditions can be treated with the devices and systems described herein. For example, the devices and systems can deliver treatments for inflammation, infection, and cancerous growths. Any number of drug combinations can be delivered using any of the devices and systems described herein.

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific methods or specific reagents, as such may vary. It is also to be understood that the terminology used herein is for the purpose of describing particular aspects only and is not intended to be limiting.

Definitions

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are pluralities of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, relative directional terms such as anterior, posterior, proximal, distal, lateral, medial, sagittal, coronal, transverse, etc. are used throughout this disclosure. Such terminology is for purposes of describing devices and features of the devices and is not intended to be limited. For example, as used herein "proximal" generally means closest to a user implanting a device and farthest from the target location of implantation, while "distal" means farthest from the user implanting a device in a patient and closest to the target location of implantation.

As used herein, a disease or disorder refers to a pathological condition in an organism resulting from, for example, infection or genetic defect, and characterized by identifiable symptoms.

As used herein, treatment means any manner in which the symptoms of a condition, disorder or disease are ameliorated or otherwise beneficially altered. Treatment also encompasses any pharmaceutical use of the devices described and provided herein.

As used herein, amelioration or alleviation of the symptoms of a particular disorder, such as by administration of a particular pharmaceutical composition, refers to any lessening, whether permanent or temporary, lasting or transient that can be attributed to or associated with administration of the composition.

As used herein, an effective amount of a compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

Pharmaceutically effective amount, therapeutically effective amount, biologically effective amount and therapeutic amount are used interchangeably herein to refer to an amount of a therapeutic that is sufficient to achieve a desired result, i.e. Therapeutic effect, whether quantitative or qualitative. In particular, a pharmaceutically effective amount, in vivo, is that amount that results in the reduction, delay, or elimination of undesirable effects (such as pathological, clinical, biochemical and the like) in the subject.

As used herein, sustained release encompasses release of effective amounts of an active ingredient of a therapeutic agent for an extended period of time. The sustained release may encompass first order release of the active ingredient, zero order release of the active ingredient, or other kinetics of release such as intermediate to zero order and first order, or combinations thereof. The sustained release may encompass controlled release of the therapeutic agent via passive molecular diffusion driven by a concentration gradient across a porous structure.

As used herein, a subject includes any animal for whom diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

As used herein, a therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

As used herein, a composition refers to any mixture. It can be a solution, a suspension, an emulsion, liquid, powder, a paste, aqueous, non-aqueous or any combination of such ingredients.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination, optionally, including instructions for use of the combination and/or other reactions and components for such use.

Eye Anatomy

FIG. 1 is a cross-sectional, schematic view of a portion of the human eye 10 showing the anterior chamber, posterior chamber and vitreous body of the eye. The eye 10 is generally spherical and is covered on the outside by the sclera 24. The bulk of the eye 10 is filled and supported by the vitreous body (referred to herein as vitreous humor or just vitreous) 30, a clear, jelly-like substance disposed between the lens 22 and the retina 26. The retina 26 lines the inside posterior segment of the eye 10 and includes the macula 32. The retina 26 registers the light and sends signals to the brain via the optic nerve. The fovea centralis is the part of the eye located in the center of the macula 32 of the retina 26 and is the region responsible for sharp central vision, for example in order to read or drive. An imaginary line passing from the midpoint of the visual field to the fovea centralis is called the visual axis 27. The hypothetical straight line passing through the centers of curvature of the front and back surfaces of the lens 22 is the optic axis 29.

The elastic lens 22 is located near the front of the eye 10. The lens 22 provides adjustment of focus and is suspended within a capsular bag from the ciliary body 20, which contains the muscles that change the focal length of the lens 22. A volume in front of the lens 22 is divided into two by the iris 18, which controls the aperture of the lens 22 and the amount of light striking the retina 26. The pupil is a hole in the center of the iris 18 through which light entering anteriorly passes. The volume between the iris 18 and the lens 22 is the posterior chamber. The volume between the iris 18 and the cornea 12 is the anterior chamber. Both chambers are filled with a clear liquid known as aqueous humor.

The cornea 12 extends to and connects with the sclera 24 at a location called the limbus 14 of the eye. The conjunctiva 16 of the eye is disposed over the sclera 24 and the Tenon's capsule (not shown) extends between the conjunctiva 16 and the sclera 24. The eye 10 also includes a vascular tissue layer called the choroid 28 that is disposed between a portion of the sclera 24 and the retina 26. The ciliary body 20 is continuous with the base of the iris 18 and is divided anatomically into pars plica and pars plana 25, a posterior flat area approximately 4 mm long.

Figure 2:
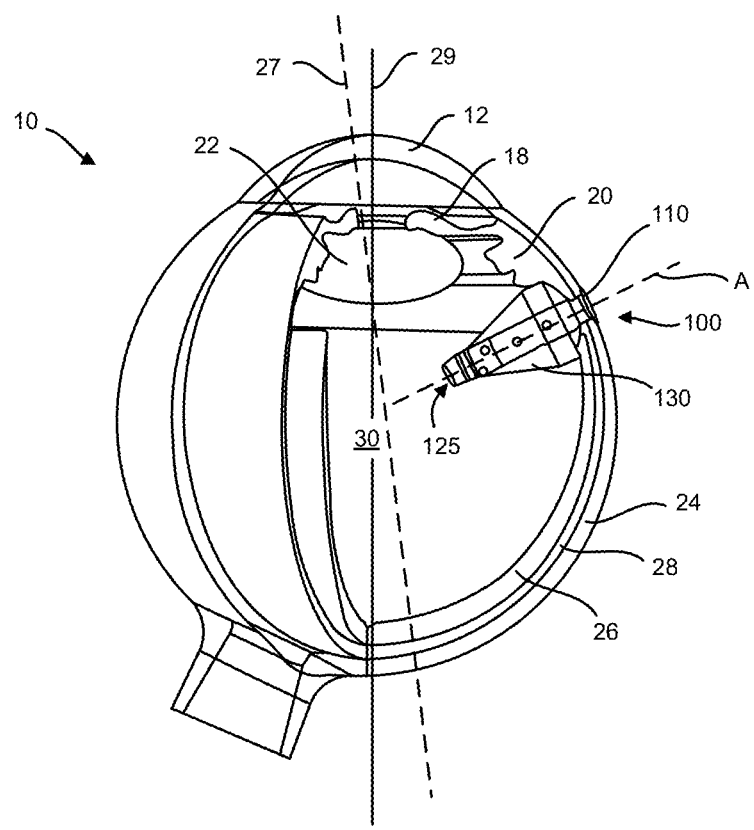
FIG. 2 is a partial, cross-sectional, schematic view of a portion of the eye having an implementation of a therapeutic device at least partially implanted within the sclera of the eye along an axis of insertion A.

The devices described herein can be positioned in many locations of the eye 10, for example in the pars plana region away from tendon of the superior rectus muscle and one or more of posterior to the tendon, anterior to the tendon, under the tendon, or with nasal or temporal placement of the therapeutic device. As shown in FIG. 2, the devices described herein can be positioned along an axis of insertion A through the sclera 24 in the pars plana region and expanded such that the device avoids interfering with the visual field, and in particular, the visual and optic axes 27, 29.

Treatment Devices

The devices described herein are referred to as drug delivery devices, treatment devices, therapeutic devices, port delivery systems, and the like. It should be appreciated that these terms are used interchangeably herein and are not intended to be limiting to a particular implementation of device over another. The devices and systems described herein can incorporate any of a variety of features described herein and the elements or features of one implementation of a device and system described herein can be incorporated alternatively or in combination with elements or features of another implementation of a device and system described herein as well as the various implants and features described in U.S. Pat. Nos. 8,399,006; 8,623,395; PCT Pat. Publication No. WO2012/019136; PCT Pat. Publication No. WO2012/019047; and PCT Pat. Publication No. WO 2012/065006. For the sake of brevity, explicit descriptions of each of those combinations may be omitted although the various combinations are to be considered herein. Additionally, described herein are different methods for implantation and access of the devices. The various implants can be implanted, filled, refilled etc. according to a variety of different methods and using a variety of different devices and systems. Provided are some representative descriptions of how the various devices may be implanted and accessed, however, for the sake of brevity explicit descriptions of each method with respect to each implant or system may be omitted.

The porous structures (also referred to herein as a drug release mechanism, release control element, RCE, or frit) as described herein can be used with a number of various different implantable therapeutic devices including one or more of those devices described U.S. Pat. Nos. 8,399,006; 8,623,395; PCT Pat. Publication No. WO2012/019136; PCT Pat. Publication No. WO2012/019047; and PCT Pat. Publication No. WO 2012/065006; the entire disclosures of which are incorporated herein by reference thereto.

Figure 3:
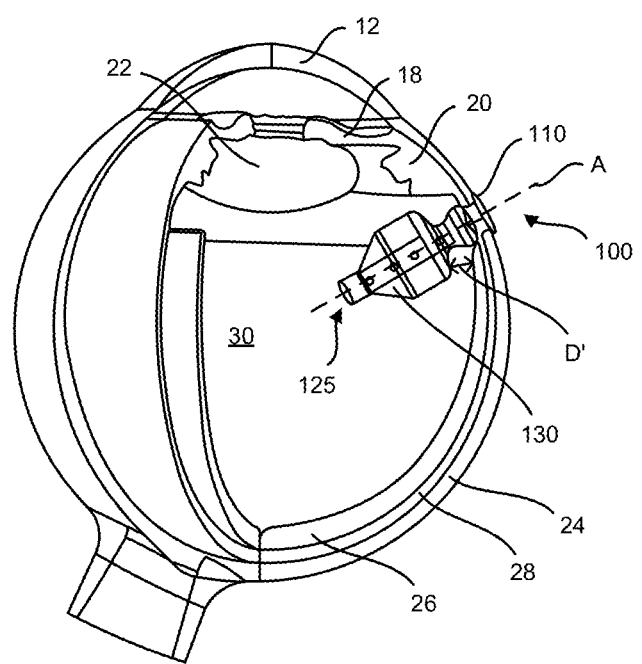
FIG. 3 is a partial, cross-sectional, schematic view of a portion of the eye having another implementation of a therapeutic device at least partially implanted within the sclera of the eye along an axis of insertion A.
Figure 4:
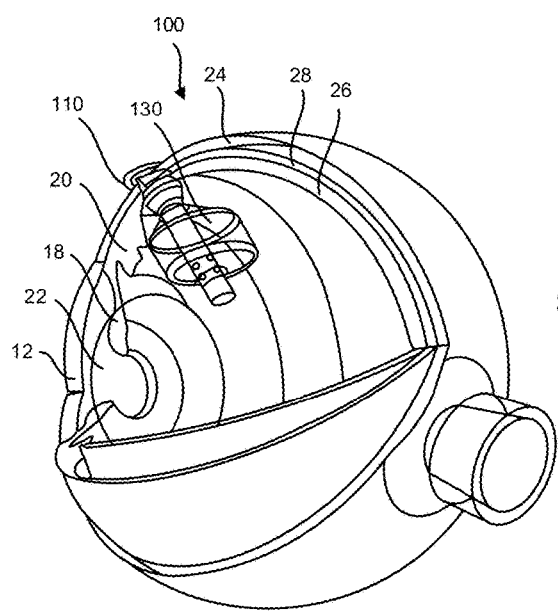
FIGS. 4 and 5 are partial, cross-sectional, schematic views of a portion of the eye having another implementation of a therapeutic device at least partially implanted within the sclera of the eye along an axis of insertion A.
Figure 5:
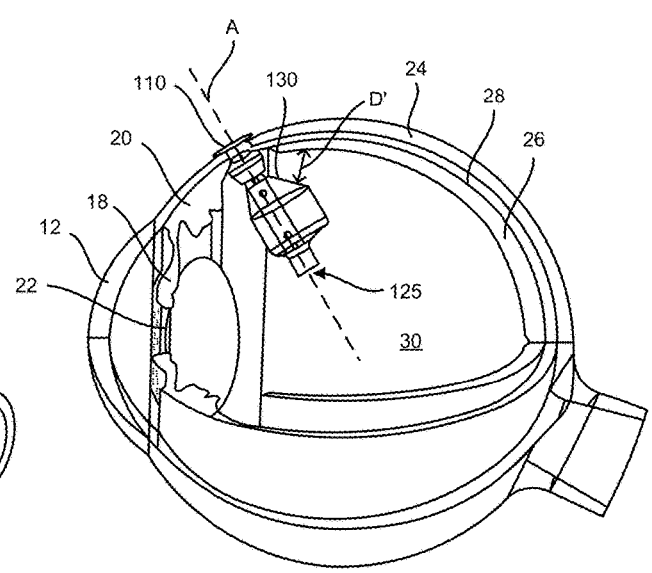
Figure 6:
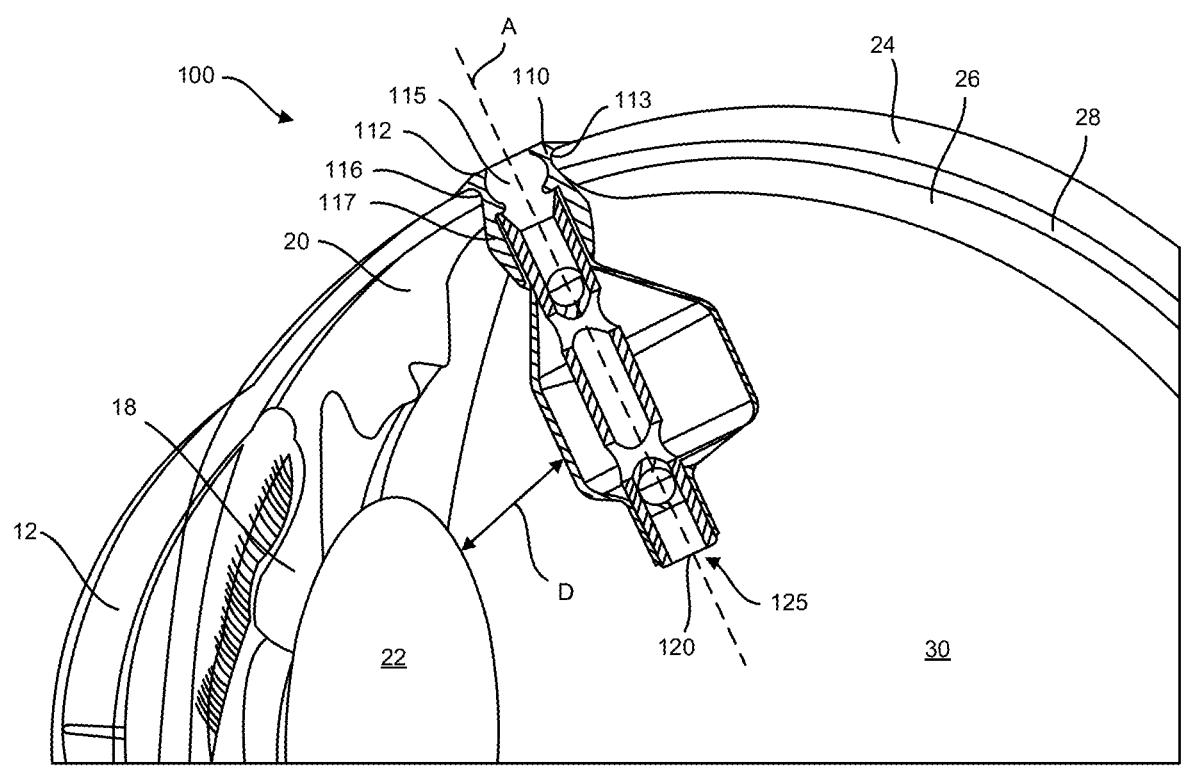
FIG. 6 is a cross-sectional view of the therapeutic device of FIG. 5.

FIGS. 2 and 3 as well as FIGS. 4-9 illustrate implementations of an expandable treatment device 100 configured to deliver one or more therapeutic agents to one or more regions of the eye 10. The device 100 can include a proximal retention structure 105 having a smooth protrusion or flange element 110, a porous drug release mechanism 120, and an expandable reservoir 130. An access port 111 can extend through the retention structure 105 and a penetrable element 115 can be positioned within at least a portion of the access port 111. The penetrable element 115 and the access port 111 allow for access to inner volume of the reservoir 130, for example, to fill, refill, and/or flush materials in the reservoir 130. In some implementations, the access port 111 can be formed by an opening through the retention structure 105 into the reservoir 130 and covered by a penetrable material and/or the penetrable element 115. The penetrable element 115 can be configured to be penetrated and resealed such that material does not leak out of the reservoir 130 following penetration of the material during in situ refilling of the reservoir 130. Alternatively, one or more regions of the flange element 110 itself can be formed of a penetrable material.

The drug release mechanism 120 can be positioned in a variety of locations within the device 100 such that the volume of the reservoir 130 is in fluid communication with the drug release mechanism 120. For example, the drug release mechanism 120 can be positioned near a distal end region of the device 100 such as within an outlet 125 of the device 100, for release of the one or more therapeutic agents contained within the reservoir 130 into the eye. The drug release mechanism 120 can also be positioned in a region of the device proximal of the distal end region. The drug release mechanism 120 can also be positioned towards a particular area to be treated, such as the retina.

The device 100 can be implanted in the eye such that at least a portion of the device 100, for example the reservoir 130, the drug release mechanism 120 and one or more outlets 125, are positioned intraocularly. In some implementations, the device 100 can be positioned so as to extend through the sclera 24 from the pars plana region so as to release the therapeutic agent into the vitreous body 30. As mentioned above, the device 100 can be positioned in the eye along an axis of insertion A (see FIG. 6). The flange element 110 can form a smooth protrusion configured for placement along the sclera 24. The flange element 110 can remain generally external to the eye to aid in retention of the device 100 while the remainder of the device 100 is at least partially positioned intraocularly. The flange element 110 can have any of a variety of shapes, for example, oval, ovoid, elliptical, circular, or other shape as will be discussed in more detail below. In some implementations, the flange element 110 can be generally curved so as to have a contour along a surface of a sphere. An outer-facing surface 112 of the flange element 110 can have a convex shape and an inner-facing surface 113 can have a concave shape such that the flange element 110 can better conform to the curvature of the eye. In other implementations, the flange element 110 can be generally flat. The edges of the flange element 110 can be generally smooth and rounded. In some implementations, when the flange element 110 is positioned such that the inner-facing surface 113 of the flange element 110 can contact the sclera 24 and the outer-facing surface 112 of the flange element 110 can be positioned under the conjunctiva 16 (not shown in FIG. 6) such that the conjunctiva 16 covers the outer-facing surface 112 of the flange element 110 and protects the therapeutic device 100. The conjunctiva 16 covering the outer-facing surface 112 of the flange element 110 can allow access to the device 100 while decreasing the risk of infection to the patient. When the therapeutic agent is inserted or injected into the device 100 through the access port of the flange element 110, the conjunctiva 16 may be lifted away, incised, or punctured with a needle to access the therapeutic device 100.

Figure 7:
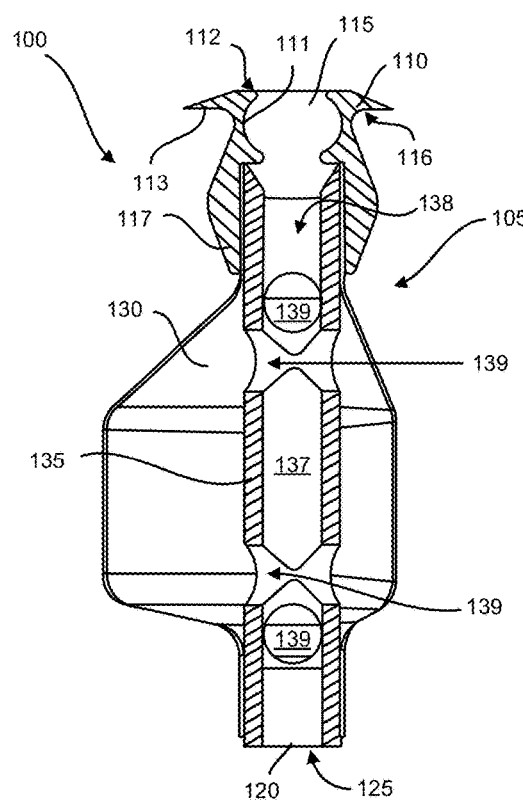
FIGS. 7 and 8 are cross-sectional views of the therapeutic device of FIG. 5.
Figure 8:
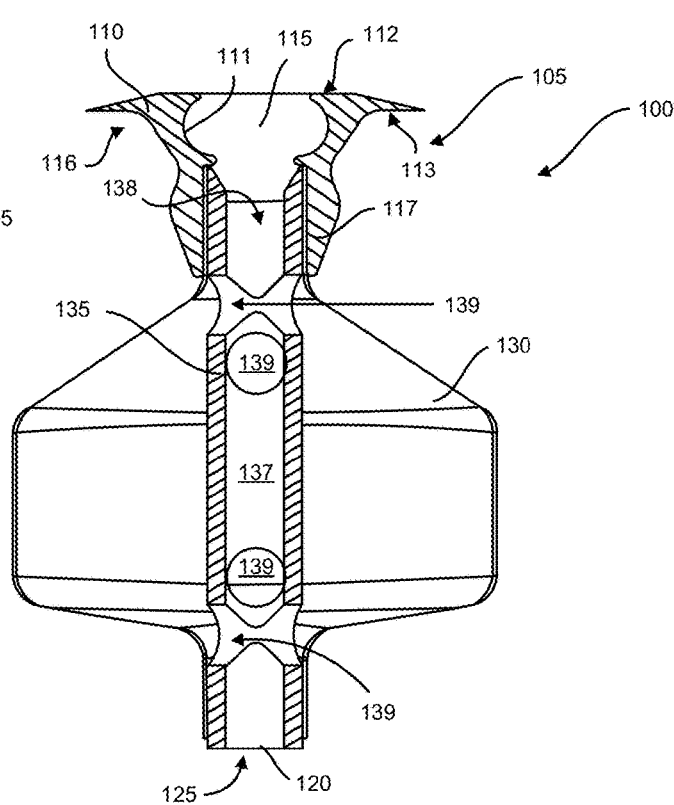

As best shown in FIGS. 7 and 8, the retention structure 105 can include the proximal flange element 110 as well as a neck positioned adjacent the flange element 110. The neck can include a proximal region 116 and a distal extension 117. The proximal region 116 of the neck can be sized along a cross-section to fit a penetration site through the sclera 24, such as an incision and/or a puncture. For example, the proximal region 116 can be narrowed relative to the flange element 110 to fit more snugly within the penetration site in the sclera 24. FIG. 7 shows a first cross-sectional view of the narrowed proximal region 116 of the neck. FIG. 8 shows a second cross-sectional view of the narrowed proximal region 116 of the neck taken along a plane orthogonal to the first cross-sectional view. The proximal region 116 of the neck can have a first cross-sectional distance across when taken along a first plane and a second cross-sectional distance across when the cross-section is taken along a second, orthogonal plane and the first cross-sectional distance can be different from the second cross-sectional distance. The distance across the proximal region 116 of the neck is shorter in the view of FIG. 7 compared to the distance across the proximal region 116 of the neck in the view of FIG. 8. In some implementations, the cross-sectional shape of the proximal region 116 of the neck can complement a shape of the incision, puncture or other penetration site through which the device 100 is inserted. The cross-sectional shape of the proximal region 116 of the neck can be elongated, including but not limited to one of a lentoid, oval, and ellipse shape. In some implementations, the cross-sectional shape of the proximal region 116 of the neck is a first curve along a first axis and a second curve along a second axis that is different from the first curve. U.S. Pat. No. 8,277,830, which is incorporated by reference herein in its entirety, describes further details regarding the geometry of the proximal region of the devices described herein.

As mentioned above, the neck of the retention structure 105 can also include a distal extension 117. The distal extension 117 of the neck can extend inside the eye a distance away from the inner surface of the sclera 24 at the penetration site. As described above and as best shown in FIG. 6, the flange element 110 can form a smooth protrusion configured for placement along the sclera 24. The proximal portion 116 of the neck can fit within the penetration site of the sclera 24 such that the tissue being penetrated is received snugly within the proximal portion 116 of the neck. The distal extension 117 can be arranged coaxial with the insertion axis A of the device and can extend a distance away from the proximal portion 116.

The distal extension 117 of the neck can provide stabilization to the penetrable region of the device 100 while eliminating contact between the expandable reservoir 130 and inner surfaces of the eye adjacent the proximal end of the device 100. FIG. 2 shows an implementation of a device 100 having a reservoir 130 that in the expanded configuration makes contact with one or more internal surfaces of the eye adjacent the proximal end of the device 100. The proximal end of the reservoir 130 can wedge against the internal tissue surfaces surrounding the penetration site through the sclera 24 and can act to stabilize the penetrable region of the device 100. In some implementations, contact between the reservoir 130 and the internal tissue surfaces is prevented to avoid irritation and/or damage of the delicate tissues of the eye. For example, as shown in FIG. 3, the proximal end of the reservoir 130 in the expanded configuration can be separated or off-set a distance D' from one or more internal tissue surfaces surrounding the penetration site. The distal extension 117 of the neck can aid in preventing contact between the device 100 and tissues adjacent the penetration site while still providing stabilization to the penetrable region of the device 100. For example, the distal extension 117 of the neck can be sufficiently long and contoured such that the reservoir 130 of the device is located a distance away from the adjacent tissue layers of the penetration site even when the reservoir 130 is in the expanded configuration. In some implementations, the distal extension 117 of the neck has a length and contour configured to prevent any portion of the device 100 distal to the extension 117 from contacting any of the internal structures of the eye except the vitreous 30 within which it is implanted. In some implementations, upon implantation and expansion of the device 100 in the eye, only the flange element 110 and the proximal region 116 of the neck come into contact with the tissue layers of the eye and the remaining portions of the device 100, such as the distal extension 117, the reservoir 130, and the drug release mechanism 120, come into contact only with the vitreous 30. The shape of the reservoir 130 in the expanded configuration can also aid in preventing this contact as will be discussed in more detail below.

As mentioned above, the devices described herein can include one or more drug release mechanisms 120. The drug release mechanism 120 can be positioned adjacent and/or within the one or more outlets 125 such that the drug release mechanism 120 can control or regulate the delivery of the one or more therapeutic agents from the reservoir 130 through the one or more outlets 125. The contents of the reservoir 130 can be delivered according to slow diffusion rather than expelled as a fluid stream. In some implementations, the one or more drug release mechanisms 120 can be disposed within a region of the reservoir 130, such as a distal end region, or a region proximal to the distal end region of the device. In some implementations, the drug release mechanism 120 can be a covering or lining having a particular porosity to the substance to be delivered and can be used to provide a particular rate of release of the substance. The drug release mechanism 120 can be a release control mechanism, including but not limited to a wicking material, permeable silicone, packed bed, small porous structure or a porous frit, multiple porous coatings, nanocoatings, rate-limiting membranes, matrix material, a sintered porous frit, a permeable membrane, a semi-permeable membrane, a capillary tube or a tortuous channel, nano-structures, nano-channels, sintered nanoparticles and the like. The drug release mechanism 120 can have a porosity, a cross-sectional area, and a thickness to release the one or more therapeutic agents for an extended time from the reservoir. The porous material of the drug release mechanism 120 can have a porosity corresponding to a fraction of void space formed by channels extending through the material. The void space formed can be between about 3% to about 70%, between about 5% to about 10%, between about 10% to about 25%, or between about 15% to about 20%, or any other fraction of void space. The drug release mechanism 120 can be selected from any of the release control mechanisms described in more detail in U.S. Pat. No. 8,277,830, which is incorporated by reference herein.

As mentioned above, the devices described herein include a reservoir 130 configured to enlarge from a generally minimally-invasive insertion configuration to an expanded configuration with an increased volume. The insertion configuration of the devices described herein has a three-dimensional shape that is relatively low profile such that the device 100 can be inserted at least partially into the eye using a small gauge device, or directly into the eye through a small incision. Many of the devices described herein can be inserted using an incision or puncture that is minimally-invasive, for example in a range of about 1 mm to about 5 mm. In some implementations, the incision is a 3.2 mm incision. It should also be appreciated that in some implementations, the device 100 can have column strength sufficient to permit the device 100 to pierce through eye tissue without an internal structural support member or members. The device can be inserted through the sclera 24 without a prior incision or puncture having been made in the eye. For example, the device can be inserted using a needle cannula member extending through an interior of the device and the drug release mechanism 120 pressed or secured inside at a distal tip of the cannula member.

Generally, when in the insertion configuration the portion of the device 100 configured to penetrate the eye (e.g. the reservoir 130) can have a smaller cross-sectional diameter compared to the cross-sectional diameter of the portion of the device 100 configured to remain external to the eye (e.g. the flange element 110). In some implementations, the cross-sectional diameter of the reservoir 130 (e.g. collapsed around a central core element 135 as will be described in more detail below) in the insertion configuration can be about 1.3 mm to about 1.5 mm in diameter, the diameter of the proximal portion 116 of the neck can be about 2.7 mm long and about 1.5 mm wide, and the flange element 110 can be about 4.5 mm long and about 3.8 mm wide. In some implementations, the device 100 can be approximately 25 gauge such that the device 100 can be inserted through a needle bore. In this implementation, the flange element 110 can be of a resilient material (such as shape memory or a flexible silicone) such that it can be housed in the needle bore during implantation and released out the distal end of the needle bore at which point the flange element 110 can retake its shape. Further, the cross-sectional shape of the eye-penetrating portion of the device 100 when in the insertion configuration can vary including circular, oval, or other cross-sectional shape. Also, when in the insertion configuration the device 100 can have a substantially uniform diameter along its entire length or the cross-sectional dimension and shape can change along the length of the device 100. In some implementations, the shape of the device 100 in the insertion configuration can be selected to facilitate easy insertion into the eye. For example, the device 100 can be tapered from the proximal end region to the distal end region.

The length of the device 100 can vary depending on where and how the device 100 is to be implanted in the eye. Generally, the length is selected so as not to impact or enter the central visual field or cross the visual axis 27 of the eye upon implantation and filling of the device 100. In some implementations, the total length of the device can be between about 2 mm to about 10 mm. In some implementations, the total length of the device can be between about 3 mm to about 7 mm. In some implementations, the length of the intraocular region of the device is about 4 mm to about 5 mm long.

Figure 9:
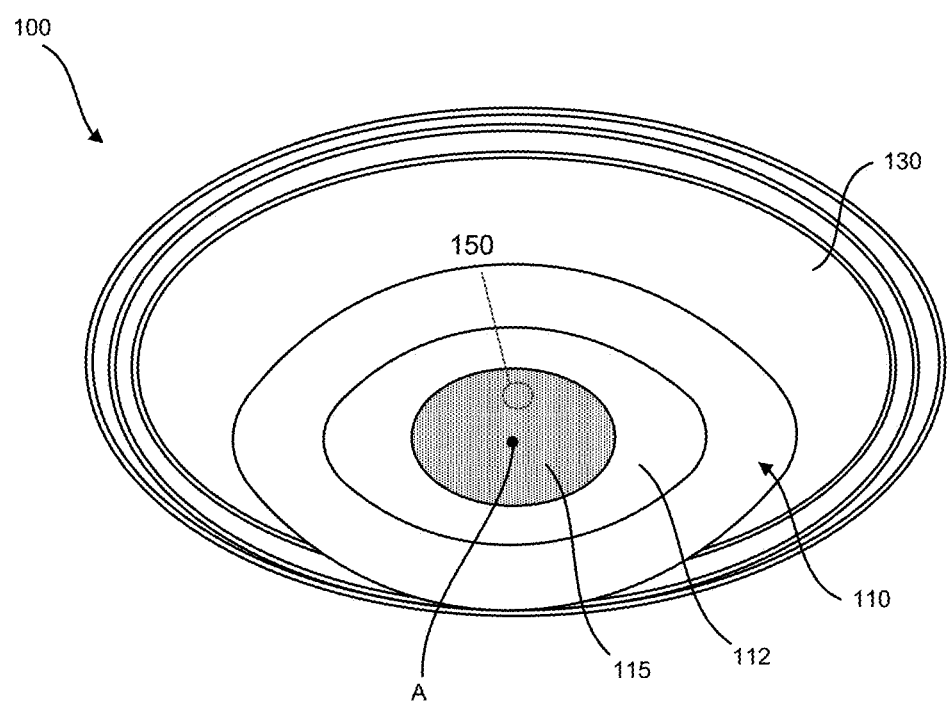
FIG. 9 is a top down view of the therapeutic device of FIG. 5.

The reservoir 130 of the devices described herein can expand into a particular contour or shape that can maximize its overall capacity while minimizing its impact on the internal eye anatomy. The insertion configuration of the reservoir 130 can have a first three-dimensional shape and the expanded configuration can have a second three-dimensional shape that is different from the first. Again with respect to FIGS. 2 and 3, the reservoir 130 in the expanded configuration can be generally symmetrical relative to the insertion axis A. In this implementation, both the first three-dimensional shape and the second three-dimensional shape can be concentric with the longitudinal axis of the device 100 and the insertion axis A. In another implementation as shown in FIGS. 4-9, the reservoir can be configured to enlarge from an insertion configuration having a first three-dimensional shape to an expanded configuration having a second three-dimensional shape, wherein the second three-dimensional shape is eccentrically positioned or generally asymmetrical relative to the insertion axis A. In this implementation, the first three-dimensional shape can be concentric with the insertion axis A and the second three-dimensional shape can be eccentric with the insertion axis A. FIG. 9 shows a top down view of a device 100 and illustrates an axis of insertion A. A plane can be drawn parallel to the axis of insertion A and orthogonal to the surface of the sclera 24 through which the device is inserted. In some implementations, more of the expanded volume of the reservoir 130 can be located on a first side of this plane than on the opposite side of this plane such that the expanded volume on the first side extends towards a posterior region of the eye or enlarges away from the lens 22 of the eye such that contact with the lens 22 is mitigated (see, e.g. FIG. 5 and also FIG. 13). Thus, a portion of the overall volume of the reservoir 130 in the expanded configuration enlarged away from the lens of the eye and is greater than the remaining portion of the reservoir 130 volume. Further, the reservoir 130 can expand such that a majority of the reservoir volume extends away from the inner surface of the sclera through which the device was inserted such that the expanded reservoir 130 avoids contacting interior surfaces of the eye that can contribute to choroidal effusions, hemorrhage or cause other unintentional contact, damage or irritation between the eye and the device 100, such as with the ciliary body or choroid. Further, when in the expanded configuration the entire reservoir 130 can remain generally outside the central visual field, such as outside the visual axis of the eye.

The expandability of the reservoir 130 from a low profile dimension for insertion to an expanded profile dimension after insertion allows for the device to be inserted in a minimally-invasive manner and also have an increased reservoir capacity. This increased reservoir capacity, in turn, increases the duration of drug delivery from the device such that the device 100 need not be refilled as frequently, and/or can reach the targeted therapeutic concentration of drug in the eye. In some implementations, the volume of the reservoir 130 can be between about 0.5 to about 100 µL. In some implementations, the volume of the reservoir 130 can be at least about 1 µL, 2 µL, 3 µL, 4 µL, 5 µL, 10 µL, 15 µL, 20 µL, 25 µL, 30 µL, 35 µL, 40 µL, 45 µL, 55 µL, 60 µL, 65 µL, 70 µL, 75 µL, 80 µL, 85 µL, 90 µL, 95 µL, 96 µL, 97 µL, 98 µL, or 99 µL or other volume.

An outer wall of the reservoir 130 can be formed of a substantially non-compliant material that is expandable yet rigid and/or non-distensible material. As such, the reservoir 130 can be filled into the expanded configuration, but the material of the reservoir 130 is configured to maintain its shape and does not stretch so as to avoid an unintentional driving force created by the memory of the wall material of the reservoir 130. In other implementations, the outer wall of the reservoir 130 can be a compliant material such that a controllable pressure can be provided by the compliant wall of the reservoir 130 up to the point of pressure equalization, for example, to provide a small initial boost of drug delivery from the reservoir after filling. Examples of expandable, non-distensible, substantially non-compliant materials are provided herein, including but not limited to PET, Nylon, and acrylics. Examples of expandable, compliant materials are also provided herein, including but not limited to silicone, urethane, and acrylics.

In some implementations, the volume of the reservoir 130 and the shape of the reservoir 130 in the expanded configuration are selected to maximize the payload capacity as well as maximizing the distance away from the lens 22 and/or the sclera 24 adjacent the penetration site. For example, in some implementations, the volume of the reservoir 130 can be 60 µL and the shape of the reservoir 130 in the expanded configuration can be D-shaped, C-shaped, elliptical, eccentric, or other shape that can extend away from the insertion axis A of the device (see FIG. 6). Thus, compared to a symmetrically expanded reservoir of smaller capacity, the eccentric or asymmetrically expanded reservoir 130 can maintain a greater distance D away from the lens 22. The reservoir 130 in the expanded configuration also can be tapered on a proximal end to maximize the distance D' the expanded reservoir 130 is off-set from the sclera 24 through which the device extends. Maintaining a greater distance D' helps to prevent contact between the expanded reservoir 130, for example the proximal end of the expanded reservoir 130, and the internal tissue surfaces surrounding the penetration site and other neighboring tissue layers of the eye such as the retina 26, choroid 28, sclera 24, ciliary body 20, and/or the lens 22. The proximal tapering of the reservoir 130 also allows for improved removal of the device 100 from the eye. The shape of the reservoir 130 can alternatively or additionally be tapered on a distal end. A distal end taper can further help the device to avoid entering the visual axis and avoid contact with certain internal structures such as the lens. Further, a smooth and gradual transition to the end of the device can also improve the ease of insertion as will be described in more detail below.

As best shown in FIGS. 7 and 8, the devices described herein can include a central core element 135 extending between the proximal end region of the device 100 and the distal end region of the device 100. The central core element 135 can be a generally cylindrical and relatively rigid element positioned around a longitudinal axis of the device 100 such that it is generally concentric with the axis of insertion A. The central core element 135 can include an inner lumen 137 and one or more openings 139 extending through a wall of the central core element 135. In some implementations, the central core element 135 can include an inlet 138 on a proximal end positioned relative to the penetrable element 115 in the access portion to receive material injected into the device, which will be described in more detail below. The inlet 138 or a portion of the central core element 135 near the inlet 138 can be surrounded by the distal extension 117 of the retention structure 105. The central core element 135 can also include an outlet located a distance away from the inlet 138 that can form the outlet 125 from the device 100, for example near a distal end of the central core element 135. The drug release mechanism 120 can be positioned within the outlet such that therapeutic agent can be released from the reservoir 130 into the eye. The central core element 135 can protect the material of the reservoir 130 from unintended penetration or puncture. For example, during filling a portion of the central core element 135 near the inlet 138 can receive a fill needle configured to inject material into the device. The central core element 135 can be formed of a material that is relatively rigid and less likely to snag on the sharp tip of the fill needle compared to the substantially non-compliant yet thinner material of the reservoir 130. Thus, the rigid core element 135 can prevent penetration of reservoir material near the inlet 138 by the needle during filling.

Figure 10:
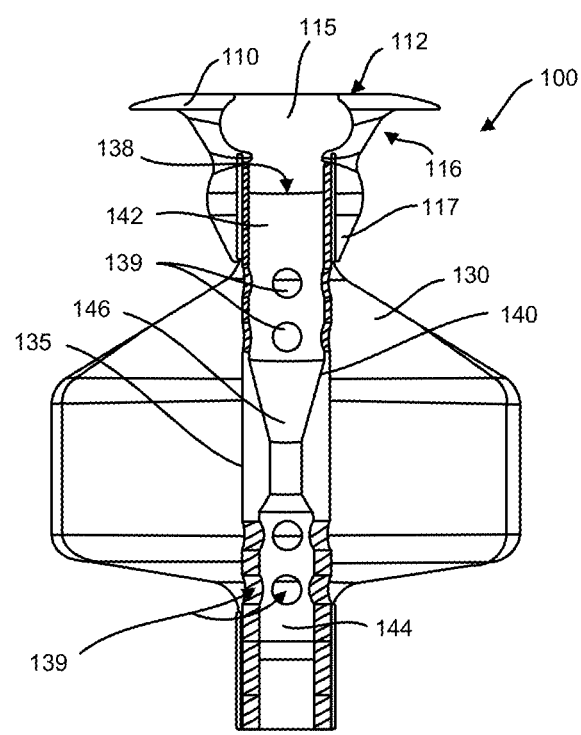
FIG. 10 is a cross-sectional view of another implementation of a therapeutic device having an implementation of a flow director.
Figure 11:
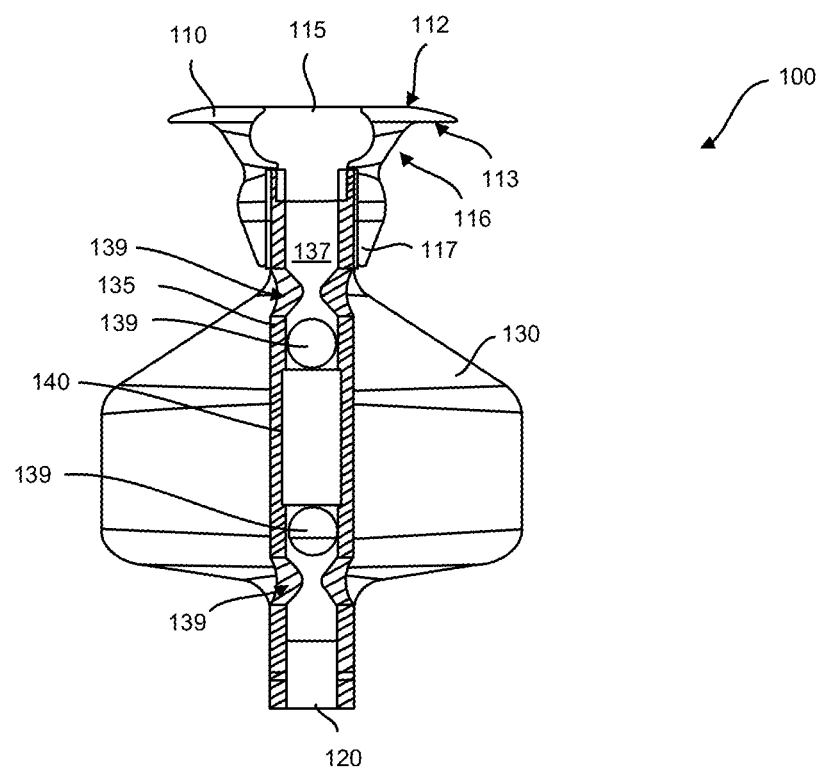
FIG. 11 is a cross-sectional view of another implementation of a therapeutic device having another implementation of a flow director.

The one or more openings 139 in the wall of the central core element 135 allow for fluid communication between the inner lumen 137 of the central core element 135 and the reservoir 130. Material introduced through the penetrable element 115 such as via a delivery element can be injected within the lumen 137 and the flow of fluid directed through the one or more openings 139 into the reservoir 130. The introduction of material into the reservoir 130 expands the inner volume of the reservoir 130 and causes the pliable walls of the reservoir 130 to move away from the longitudinal axis of the device and/or move away from the central core element 135. Expansion of the reservoir volume changes the reservoir from the initial, insertion configuration to the expanded configuration, which will be described in more detail below. Optimizing the size of the one or more openings 139 in relation to the diameter of the inner lumen 137 can help to direct flow through the central core element 135 through the one or more openings 139 into the reservoir 130. The central core element 135 can also include a flow director 140 to facilitate filling of the reservoir 130 and increase efficiency of filling (see FIG. 10). In some implementations, the flow director 140 can include a first cylindrical region 142 coupled to a second cylindrical region 144 by a funnel shaped region 146 to direct flow through the one or more openings 139. The first cylindrical region 142 can be positioned proximal to the second cylindrical region 144 the second cylindrical region 144. The first cylindrical region 142 can have a larger cross-sectional diameter than the second cylindrical region 144. Further, the one or more openings 139 of the flow director 140 can be smaller in size than in an implementation of the device without a flow director 140. In another implementation, the flow director 140 positioned within the inner lumen 137 of the central core element 135 can be a penetrable barrier, for example an element through which a delivery element extends (see FIG. 11). In this implementation, the flow director 140 can be a silicone element that has an outer diameter sized and shaped to wedge within the inner lumen 137 of the core element 135. For example, the flow director 140 that is a penetrable element can be penetrated by a fill/refill needle or other delivery element such that the device 100 can be filled/refilled from the bottom up. The material can be initially injected in a distal end region of the device until the proximal end region of the device is also filled and expanded. The fill/refill needle is described in more detail below. Refill efficiency in a device having no flow director 140 or core element 135 with openings 139 optimized to inside diameter of the central core element 135 relies on fluid densities to enable bottom-up filling and/or relatively high volume exchanges to allow for substantial mixing. The devices described herein having a flow director 140 or other core structure with optimized openings 139 can leverage paths of least resistance for evacuation of pre-existing materials from the device being filled improving refill efficiency at lower refill volumes for example, by preventing backflow and/or directing bottom-up or bottom-first filling.

As mentioned above, the treatment devices described herein can be held by an insertion tool and inserted through the puncture or incision into the target region. As such, the distal end region of the devices can be shaped in order to ease initial wound entry. A distal end region of the device having a larger diameter and/or a flatter distal tip can be more difficult to find and insert through an incision or puncture as small as 3.2 mm. Further, abrupt edges in the outer contour of the device due to bonding between structural elements of the device (e.g. where a distal edge of the reservoir material bonds to the central core element) can negatively impact tissue entry. In some implementations, the distal end region of the treatment device is beveled, tapered or has a bullet-point tip or other element such that it smoothly penetrates the tissue during implantation.

Figure 26A:
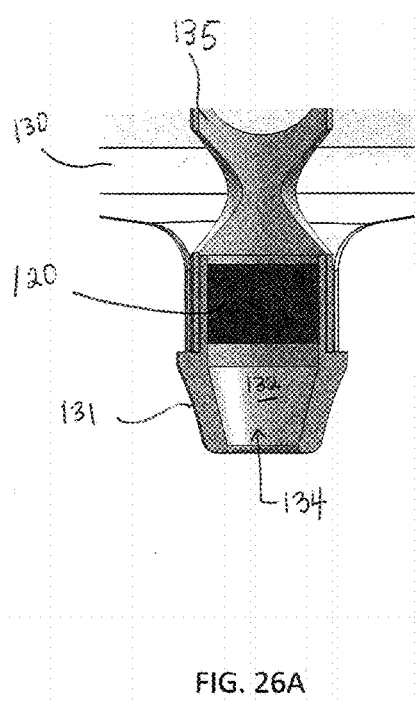
FIGS. 26A-26C are cross-sectional views of the distal end region of various implementations of a treatment device.
Figure 26B:
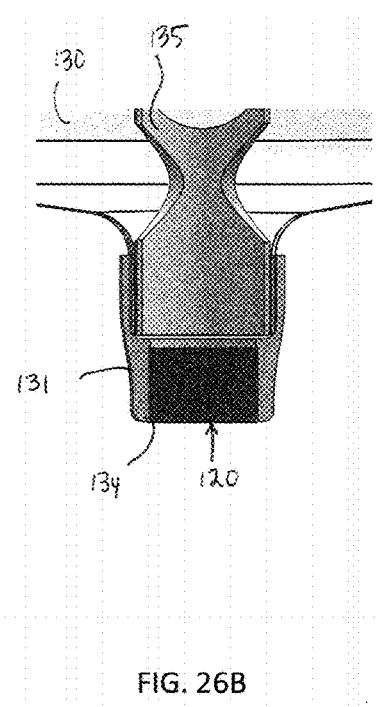
Figure 26C:
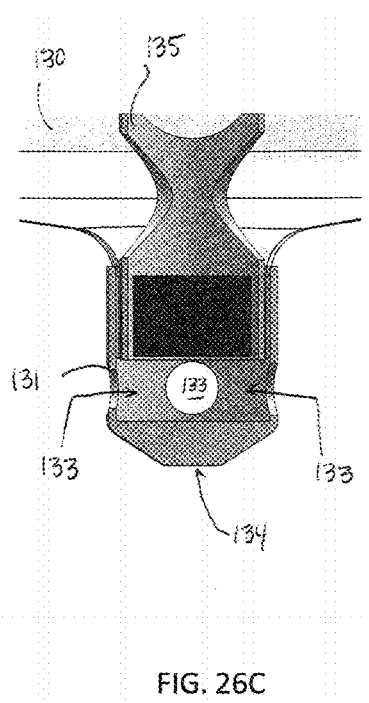

In some implementations, the distal end of the treatment device can have a sleeve 131 associated with it, for example inserted over it or inside a region of the distal end (see FIGS. 26A-26C). In some implementations, the sleeve 131 is coupled to an internal region of the distal end of the device 100 such that a proximal portion of the sleeve 131 receives the drug release mechanism 120 and inserts within a distal outlet of the central core element 135. The sleeve 131 can receive the drug release mechanism 120 within an internal cavity 132 that extends from a proximal end region of the sleeve 131 through to a distal outlet 134 such that diffusion of drug from the reservoir 130 through the drug release mechanism 120 is not blocked by the sleeve 131. Edges of the sleeve 131 surrounding the internal cavity 132 can be rounded to reduce coring or catching of tissue inside the internal cavity 132. The sleeve 131 can be a polymer material having a tapered geometry. A distal portion of the sleeve 131 can extend beyond the distal end of the device 100 such that the sleeve 131 forms a tapered tip (see FIG. 26A). It should be appreciated, however, that the sleeve 131 need not extend beyond the distal end of the device 100. The sleeve 131 can taper from the 0.05" diameter near where the drug release mechanism 120 is positioned in the internal cavity 132 of the sleeve 131 down to approximately 0.03" at the distal tip of the sleeve 131. The drug release mechanism 120 can be fused to the internal cavity 132 of the polymer sleeve 131, which in turn can be inserted and attached to the central core element 135 (see FIG. 26A). The distal edge of the material forming the reservoir 130 can then be attached around the central core element 135.

In other implementations, the sleeve 131 can insert over a distal end region of the treatment device 100 (see FIG. 26B). For example, the distal edge of the material forming the reservoir 130 can be bonded over the central core element 135 and the two components together inserted within a proximal region of the internal cavity 132 of the sleeve 131. The sleeve 131 can smooth the distal tip of the device 100 and eliminate snagging of the tissue against connection points between the reservoir 130 and the central core element 135 providing for a smoother entry of the device 100 through the incision. The coupling between the sleeve 131 over the distal end region can further provide support to the bond between the distal end of the reservoir 130 and the central core element 135. As such the sleeve 131 could, but does not necessarily have a smaller outer diameter than the distal end region of the treatment device 100. Further, the rounded edges can improve finding and insertion into the incision.

In a further implementation, the sleeve 131 can insert over the distal end of the treatment device 100 as described above (see FIG. 26C). The sleeve 131 can extend distal to the device and have a tip with an outer diameter that is approximately 0.02". As with prior implementations, the sleeve 131 can have rounded edges to reduce coring and one or more side outlet holes 133 in addition to or in alternative to the distal outlet 134 through which drug can escape the internal cavity 132 of the sleeve 131.

As mentioned above, the central core element 135 can be bonded at a proximal end to an upper portion of the reservoir 130 and at a distal end to a lower portion of the reservoir 130. The bond between the central core element 135 and the reservoir 130 as well as the central core element 135 and the drug release mechanism 120 can be achieved by adhesives such as a two-part epoxy like Epotech 301. In some implementations, thermal fusing between the components is used. For example, if the central core element 135 and the reservoir material can both be made from thermally bondable materials, such as nylon or polysulfone (PSU), the two may be thermally bonded together using heat and compression providing a simpler manufacturing process and more reliable bond than adhesive. The central core element 135 also can be formed of a metal material and designed to accept the flow of plastic such that it can be joined to the reservoir using heat and compression despite not be formed of the same thermally bondable material. In some implementations, the distal and/or proximal region of the central core element 135 can incorporate a plurality of small holes to accept the flow of a polymer material such as a small hole pattern laser drilled into the core. If the reservoir material and the central core element are made from similar materials or the core has features designed to accept the flow of a polymer material an ultrasonic welding process can be used to provide energy required to create the bond between them. In further implementations, the central core element 135 can be formed of a thermoplastic that can allow for the development of an over-molding process between the drug release mechanism 120 to create a bond joint between the drug release mechanism 120 and the central core element 135 at the distal end of the device.

Figure 12:
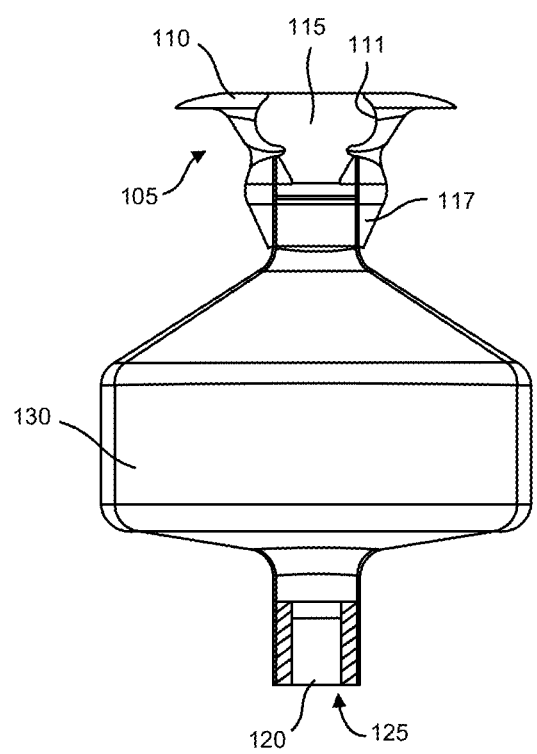
FIG. 12 is a cross-sectional view of another implementation of a therapeutic device.

It should be appreciated that the devices described herein need not include a flow director 140 or a central core element 135. For example, FIG. 12 shows an implementation of a device 100 having an expandable reservoir 130 coupled on a proximal end to a retention structure 105 having a flange element 110, a penetrable barrier 115 positioned within an access port 111 and a distal extension 117. The expandable reservoir 130 is coupled on a distal end region to an outlet 125 having a drug release mechanism 120 positioned therein. However, there is no central core element 135 or flow director 140 incorporated. The material of the reservoir 130 can provide sufficient rigidity to the device such that it can be inserted through a penetration site along an axis of insertion A without collapsing in on itself or warping away from the insertion configuration or axis of insertion A. In some implementations, the material of the reservoir 130 is Polyethylene terephthalate (PET) and has a wall thickness in the range of about 0.0005 mm to about 0.05 mm such that the device has column strength and is generally rigid enough to insert into the eye without a central core element or flow director. In some implementations, the devices described herein can be implanted using a stylet or other rigid, longitudinal element that can be inserted within a region of the reservoir at the time of placement and then removed once the necessary column strength has been imparted and the device has penetrated through the sclera. The material of the reservoir 130 can also include Urethane, Nylon, Pebax, Polyurethanes, cross-linked polyethylene, FEP, PTFE, and similar materials and blends of materials. The materials may also include multiple layers of the above materials and other materials known in the art for manufacturing expandable elements.

Figure 13:
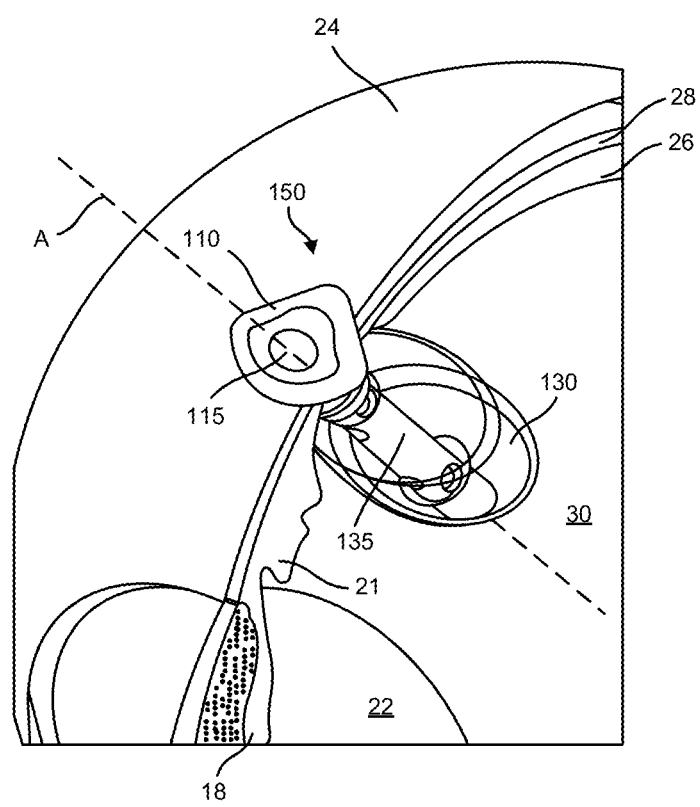
FIG. 13 is a partial, cross-sectional perspective view of an implementation of a flange element on a therapeutic device.

As discussed above, the device can include a proximal retention structure 105 having a smooth protrusion or flange element 110 configured to remain generally external to the eye to aid in retention of the device 100 when the remainder of the device 100 is implanted intraocularly. In some implementations, the flange element 110 can be designed to provide an identifiable orientation of the device 100 for implanting in the eye such that the direction of expansion of an eccentrically expanding reservoir 130 is predictable and according to a desired orientation. The reservoir 130 once implanted within the vitreous 30 may not be directly visualized. Thus, an orientation indicator 150 on a portion of the device 100, such as the flange element 110, that can be visualized from outside the eye allows a user to know the expansion of the reservoir 130 will be in the correct plane. For example, FIG. 9 illustrates an orientation indicator 150 that is a dot or other visual indicator on an upper surface of the flange element 110. FIG. 13 illustrates an orientation indicator 150 that is a shape of the flange element 110 that indicates the orientation of the eccentric volume of the reservoir. For example, because the expandable reservoirs 130 can be designed to expand along a particular orientation relative to the longitudinal axis of the device and/or the insertion axis A, the relative orientation of that portion of the expandable reservoir 130 around the axis A can be critical in ensuring the device does not impinge on certain intraocular structures. In some implementations, the flange element 110 can incorporate a mark or other orientation indicator 150 on an upper surface 112 that is visible to a user to indicate orientation of reservoir filling. The orientation indicator 150 can be any of a variety of shapes, colors or combination of shapes and colors providing guidance regarding where the eccentric volume is located. Alternatively or additionally, the orientation indicator 150 can be the shape of the flange element 110 itself. For example, the flange element 110 can be shaped in such a way to provide directional guidance to a user for implantation of the device. The flange element 110 can have a variety of shapes such as an ovoid, elliptical, polygonal, triangular, or diamond shape or other shape such as an arrow having a side or angle or portion that indicates where the reservoir 130 is designed to have a greater expansion compared to another side of the reservoir 130. FIG. 13 illustrates a flange element 110 having a particular shape indicating orientation of the eccentric region of the reservoir 130. Upon filling, the orientation indicator 150 will indicate to a user the portion of the reservoir 130 that will expand away from one or more internal structures of the eye, such as the lens 22. It should be appreciated that the flange element 110 can be keyed or configured to couple with a fill device having keyed features that also provides visual feedback to the user regarding the orientation of the eccentric volume of the device prior to fill or refilling.

Figure 14:
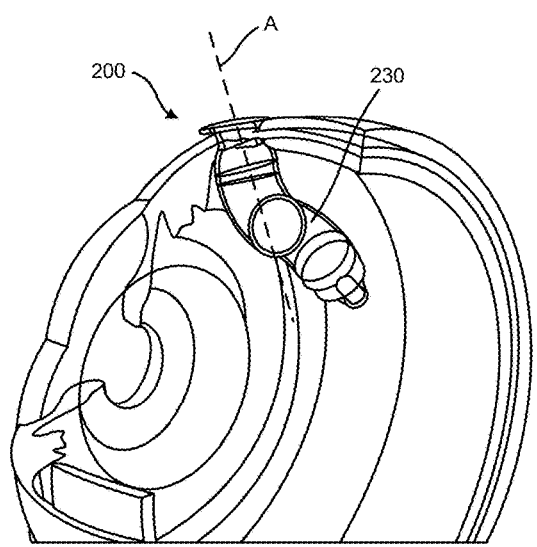
FIGS. 14-16 illustrate various views of another implementation of an expandable therapeutic device.
Figure 15:
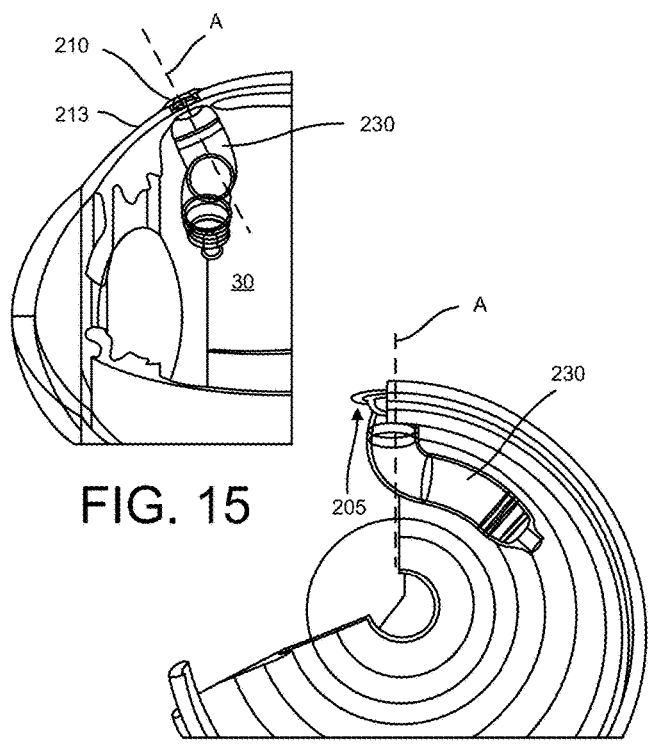
Figure 16:
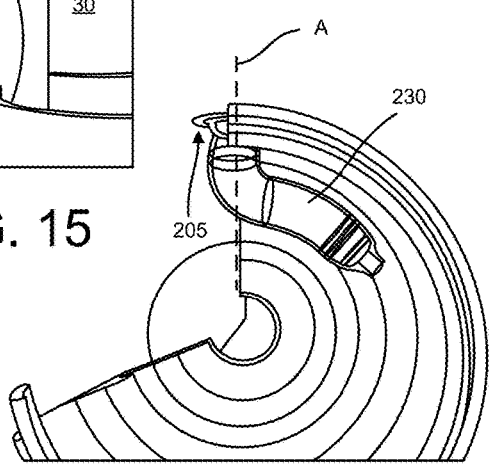

The devices described herein can incorporate expanding reservoirs that are also symmetrically distributed in the expanded configuration. As previously shown in FIGS. 2 and 3, the reservoir 130 can enlarge from the insertion configuration to an expanded configuration such that the volume of the reservoir 130 is symmetrically distributed about the longitudinal axis of the device as well as the axis of insertion A. In another implementation, the devices described herein can have expanded configurations that are symmetrically distributed, but the overall shape of the device itself can be formed into a curvilinear or other shape that is not aligned with the axis of insertion A. FIGS. 14-16 show an implementation of a device 200 having a reservoir 230 that expands generally symmetrically, but the implanted portion of the device 200 (i.e. the portion of the device 200 distal to the proximal retention structure 205) is shaped to curve away from the axis of insertion A. In some implementations, the portion of the device 200 within the vitreous 30 can extend generally perpendicular to the inner-facing surface 213 of the flange element 210 prior to implantation and filling. However, after implantation and filling, the device 200 can be formed or shaped such that the device 200 as a whole is off-axis relative to the insertion axis A. The device 200 is positioned generally such that even the distal-most region of the device 200 remains outside the visual axis of the eye and/or avoids contact with certain structures of the internal eye anatomy as described above. In some implementations, the device 200 in the expanded configuration is shapeable into a curvilinear shape that remains outside the visual axis of the eye. The device 200 can have an insertion configuration in which the reservoir 230 is collapsed around a longitudinal axis of the device into a minimally-invasive dimension for insertion through the sclera. After insertion through the sclera, the implanted portion of the device 200 distal to the retention structure 210 can be pre-shaped according to a desired angle and/or curve. For example, the region of the device 200 implanted in the vitreous 30 can be angled away from the insertion axis A. In another implementation, the region of the device 200 implanted in the vitreous 30 can be formed into a curve away from the insertion axis A, for example a curve that approaches the curve of the eye (see FIG. 16). Once the distal end region of the device 200 is shaped into the desired shape, the reservoir 230 can then be filled with therapeutic material to expand the reservoir 230 into the expanded configuration. The expanded configuration can be a symmetrically distributed expanded configuration such as that shown in FIGS. 14-16. Alternatively, the expanded configuration of the device 200 can be asymmetrically expanded or eccentrically expanded as described above such that the device 200 does not impinge upon certain internal structures of the eye and/or the visual field, visual axis, and/or optical axis. It should also be appreciated that the reservoir 230 can be a rigid, non-expandable configuration similar to those described in U.S. Pat. No. 8,277,830, which is incorporated by reference herein.

Figure 17:
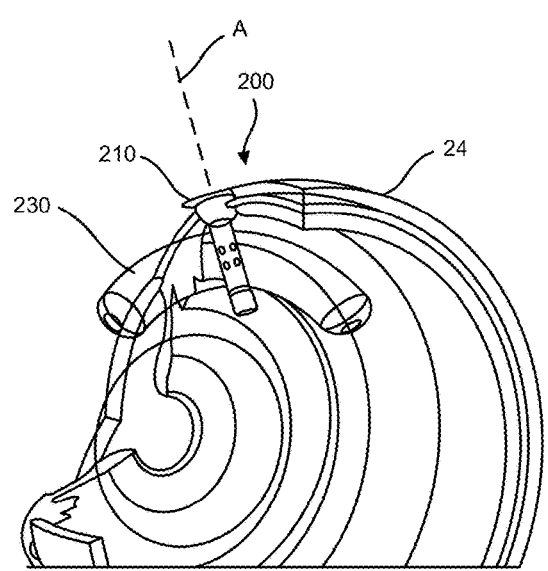
FIGS. 17-18 illustrate various views of another implementation of an expandable therapeutic device.
Figure 18:
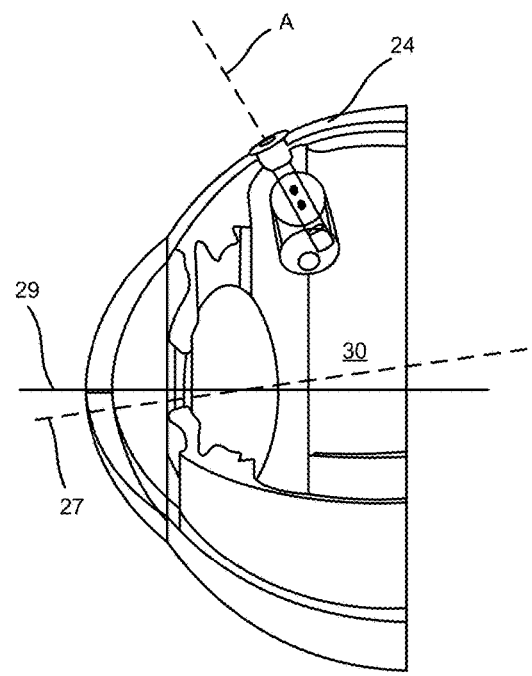
Figures 19A, 19B, 19C, 19D:
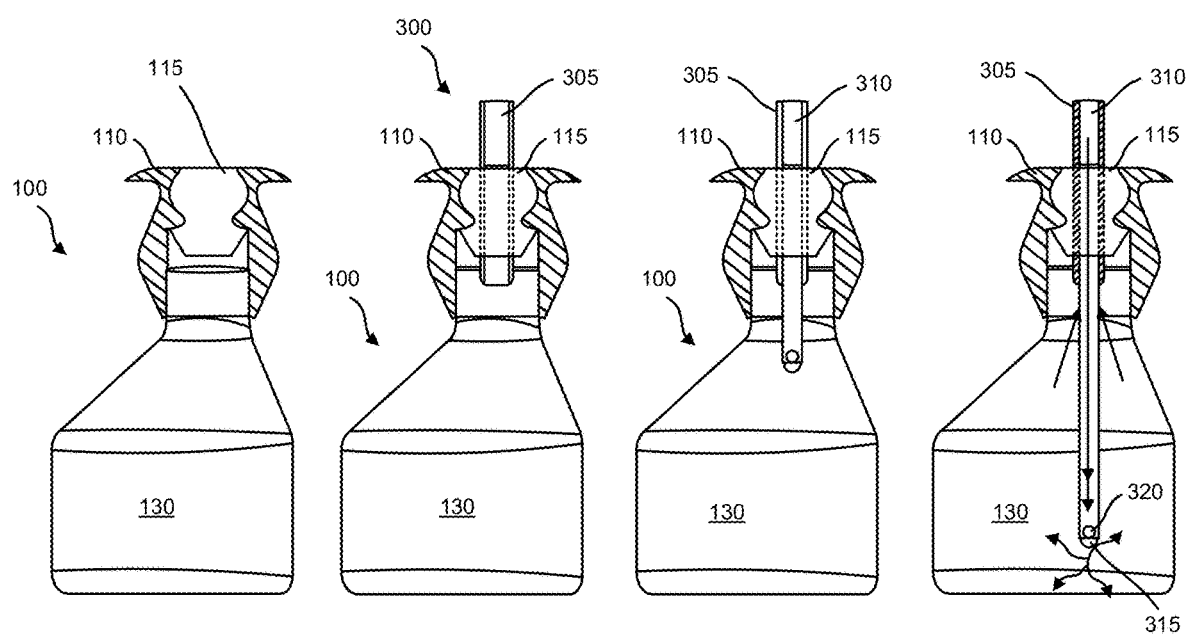
FIGS. 19A-19D illustrate sequential views of a device inserted for filling of a therapeutic device.

FIGS. 17-18 illustrate another implementation of a device 200 having a reservoir 230 that expands generally symmetrically. The implanted portion of the device 200 (i.e. the portion of the device 200 distal to the proximal retention structure 205) is shaped to curve away from the axis of insertion A upon filling. The device 200 can have an insertion configuration configured to be inserted through the sclera 24 into the vitreous 30 along the axis of insertion A and in a generally, minimally invasive manner. After insertion, the device 200 can be filled to expand the reservoir 230 into the expanded configuration. In the expanded configuration, the reservoir 230 can extend along a curvilinear path around a perimeter of the eye such that the device 200 does not impinge upon the visual field and/or the visual or optic axes 27, 29 (see FIG. 18). It should be appreciated that the device 200 can be pre-shaped and filled to expand the reservoir 230 afterwards. It should be appreciated that the drug release mechanism can be positioned within any of a variety of outlets of the device. For example, each of the reservoir portions extending away from the insertion axis can have an outlet each with a drug release mechanism positioned within or near the outlet or each of the reservoir portions can direct therapeutic agent through a single outlet, for example, an outlet positioned near a distal end of the device along the central axis of the device. Further, a wall of the reservoir can include highly calibrated perforations as the drug release mechanism.

Methods of Use

It should be appreciated that the treatment devices described herein can be used in a variety of locations and implanted in a variety of ways. The implantation method and use of the treatment devices described herein can vary depending on the type of treatment device being implanted and the intended location and drug for treatment. As will be described in more detail below, the treatment devices described herein can be primed, implanted, filled, refilled, and/or explanted using one or more devices.

In one implementation of treatment device implantation, a sclerotomy is created according to conventional techniques. The sclerotomy can be created posterior to an insertion site of the treatment device through the sclera 24 or the sclerotomy can be created directly above the insertion site of the post through the sclera 24. The conjunctiva 16 can be dissected and retracted so as to expose an area of the sclera 24. An incision in the conjunctiva 16 can be made remote from the intended insertion site of the treatment device. A scleral incision or puncture can be formed. The scleral incision or puncture can be made with a delivery device tool or using a distal tip of the treatment device, as described above. In some implementations, the treatment device is implanted using sutureless surgical methods and devices. In other implementations, the treatment device can be positioned sub-sclerally such as under a scleral flap. The post can be inserted into the eye (such as within the vitreous or the anterior chamber, etc.) until at least one of the outlets is positioned within or near the target delivery site and, if a flange element is present, until the inner-facing surface of the flange element can abut an outer surface of the eye. An additional fixation element can be used such as a suture or other element if needed following implantation of the treatment device in the eye. The treatment device can remain in position to deliver the one or more therapeutic agents to the eye for a period of time including, but not limited to 1, 2, 3, 4, 5, 10, 15, 20, 25 days or any number of days, months and year, up to at least about 3 years. After the therapeutic agent has been delivered for the desired period of time, the treatment device can be refilled for further delivery or removed.

Generally, the implementations of the treatment devices described herein contain drug solutions, drug suspensions and/or drug matrices. The treatment devices described herein can also contain therapeutic agents formulated as one or more solid drug core or pellets formulated to deliver the one or more therapeutic agents at therapeutically effective amounts for an extended period of time. The period of time over which the treatment device delivers therapeutically effective amounts can vary. In some implementations, the treatment device is implanted to provide a therapy over the effective life of the device such that refill of the device is not necessary.

FIGS. 19A-19D show a generalized tool 300 designed to prime, fill and/or refill the treatment devices described herein. The tool 300 can include a trocar introducer cannula 305 having an internal lumen through which an internal fill cannula 310 can extend. The introducer cannula 305 can extend through the penetrable element 115 in the proximal region of the device 100 until the distal end of the cannula 305 enters a proximal end region of the reservoir 130 (see FIG. 19B) and/or the proximal end of the central core element 135, if present. A region of the tool 300 can have a hard stop to prevent the distal tip 315 from extending too far into the reservoir 130. The internal fill cannula 310 can extend through the internal lumen of the introducer cannula 305 and into at least the proximal end region of the reservoir 130 (see FIG. 19C). The fill cannula 310 can extend further into the reservoir 130 towards a distal end region of the reservoir 130. The overall length of the fill cannula 310 can be selected based on the treatment device with which it will be used such that the fill cannula 310 can extend towards a distal end region of the reservoir 130 or the central core element 135, if present. Or if the device includes a flow director 140, the fill cannula 310 can have a length configured to extend through at least a region of the flow director 140. The fill cannula 310 can include a distal tip 315 that is blunted and has an opening 320 through which material may flow out of the fill cannula 310 (see FIG. 19D). The flow of material through the fill cannula 310 and out the opening 320 near the distal tip 315 allows for filling of the reservoir 130 in a bottom-up manner. A distal end region of the introducer cannula 305 can be configured to receive pre-existing material from the reservoir 130 such that it can be flushed out from the reservoir 130 upon filling with new material through the fill cannula 310. This in combination with a flow director 140 can increase refill efficiency. The tool 300 can incorporate one or more features of other refill devices described, for example, in U.S. Pat. Nos. 8,399,006; 8,623,395; U.S. Publication No. 2013/0324918; and U.S. Publication No. 2013/0165860, which are each incorporated in their entireties herein.

Figure 20A:
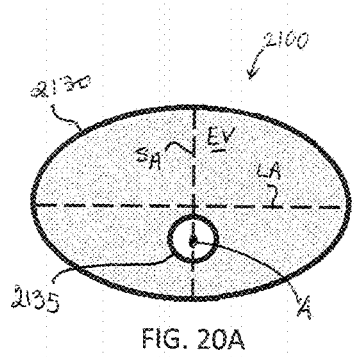
FIGS. 20A-20F schematic, top-down views of an implementation of a treatment device having an expandable, asymmetric reservoir in various stages of folding.
Figure 20B:
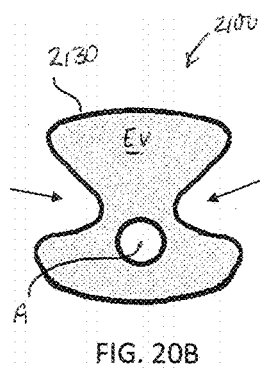
Figure 20C:
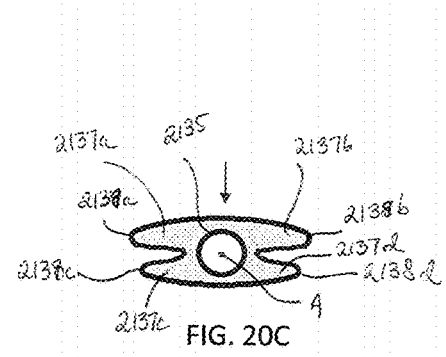
Figure 20D:
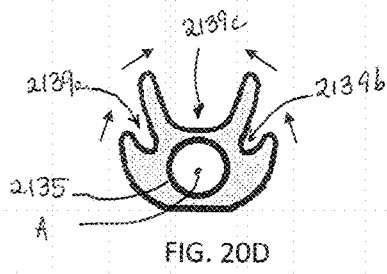
Figure 20E:
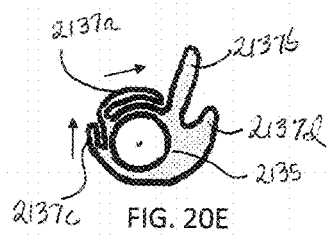
Figure 20F:
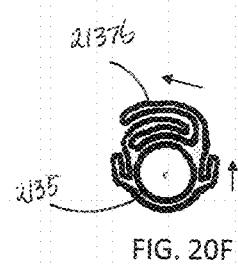

As described herein the treatment device can have an expandable reservoir formed of a generally non-compliant material. The reservoir can be folded down so that it fits within the internal volume of a delivery element and deployed reliably upon expansion. FIGS. 20A-20F show in schematic, top-down views an implementation of a treatment device 2100 in various stages of reservoir folding. The treatment device 2100 has a reservoir 2130 surrounding in an eccentric manner an axis A of the device. For the sake of simplicity, the folding of the reservoir 2130 will be described in terms of this axis A. The axis A can be coaxial with a central axis of the central core 2135, if present, although it should be appreciated that the central core element 2135 need not be present for the device to be folded as described below. The reservoir 2130 can be eccentric in that more of the expanded volume of the reservoir 2130 can be located on a first side of a plane drawn parallel to the axis A than on the opposite side of the plane such that the reservoir 2130 expands asymmetrically relative to the axis A. As shown in FIG. 20A, the asymmetric reservoir 2130 in an unfolded configuration can have a central region with an oval cross-sectional shape having a long axis LA and a short axis SA. An eccentric volume EV of the expanded portion of the reservoir 2130 can be located on a first side of the plane drawn parallel to the axis A. FIG. 20B shows a first step in folding the reservoir 2130 during which opposing regions of the reservoir 2130 along the long axis LA are urged inward towards one another creating a narrowed pinched region near a center of the reservoir volume. Opposing regions of the reservoir 2130 along the short axis SA can then be urged towards one another and toward the central axis A (see FIG. 20C). This configuration creates four folds or pleats 2137a, 2137b, 2137c, 2137d in the material of the reservoir 130, two on either side of the axis A extending outward along the long axis LA of the reservoir 130. Each pleat 2137a, 2137b, 2137c, 2137d can have a pleat end 2138a, 2138b, 2138c, 2138d. Adjoining pleats 2137a, 2137c can form a first trough 2139a and adjoining pleats 2137b, 2137d can form a second trough 2139b. The pleat ends 2138a, 2138c of a first two of the pleats 2137a, 2137c can be urged in a clockwise manner relative to the axis A toward the eccentric volume EV side and the pleat ends 2138b, 2138d of a second two of the pleats 2137b, 2137d can be urged in a counter-clockwise manner relative to the axis A toward the eccentric volume EV side forming a third trough 2139c (see FIG. 20D). Pleat end 2138a can be urged in the clockwise direction until pleat 2137a folds down inside third trough 2139c. Pleat 2137b folds up against the central core 2135 onto the first trough 2139a (FIG. 20E). Pleat end 2138c is then urged in the counter-clockwise manner relative to the axis A until pleat 2137c overlies pleat 2137a. Pleat 2137d folds up against central core 2135 onto second trough 2139b. The asymmetric shape of the reservoir 2130 relative to the axis A of the device and the folding process results in pleats 2137a, 2137c forming longer "wings" of material relative to the pleat 2137b, 2137d. Further, this configuration results in pleat 2137c overlying pleat 2137a while the pleat 2137b, 2137d being pressed against the sides of the central core 2135. It should be appreciated, however that pleat 2137c can fold into the third trough 2139c and pleat 2137a overlie pleat 2137c. Generally, two of the pleats that are longer (i.e. the pleats on the eccentric volume EV side of the reservoir) can overlap at least a portion of their length while two of the pleats that are shorter (i.e. the pleats on the opposite side) do not overlap. It should be appreciated that the folding described above can also be applied to compliant materials in as much as necessary to deal with any excess material that may be needed to produce the asymmetric region of the reservoir.

The treatment devices described herein can be primed and inserted using one or more devices described in U.S. Publication No. 2015/0080846, which is incorporated by reference herein. In some implementations, the folded down treatment device 2100 can be held within a priming tool 2200. FIGS. 21A-21B show an unloaded priming tool 2200 and a close-up of the priming tool 2200 loaded with a treatment device 2100, respectively. The priming tool 2200 can be a separate tool or can be integrated with a delivery system used to fill and/or implant the treatment device 2100. In some implementations, a user can hold the priming tool 2200 by handles 2205 on a proximal end of the tool 2200 and operatively coupled to opposing clamshells 2210 on a distal end. The handles 2205 can have a reverse tweezer type of actuation mechanism such that the clamshells 2210 are biased in a closed position against one another and a squeeze inward moves the opposing clamshells 2210 a distance away from one another. The clamshells 2210 each can have a recessed internal geometry configured to contain at least a portion of the treatment device 2100. For example, one of the clamshells 2210 can have a first recess portion and the second of the clamshells 2210 can have a second recess portion that when the clamshells 2210 are in a closed position together the recess portions form a cavity 2215 having a shape substantially the same as an outer contour of the treatment device 2100. The priming tool 2200 can hold the treatment device 2100 within the cavity 2215 formed by the opposed recess portions and the folded pleats of the reservoir 2130 can be constrained and prevented from expanding, particularly during priming as will be described in more detail below. The clamshells 2210 can be formed of a substantially clear material for optimal viewing and/or visual indications during priming of the treatment device 2100.

Figure 21C:
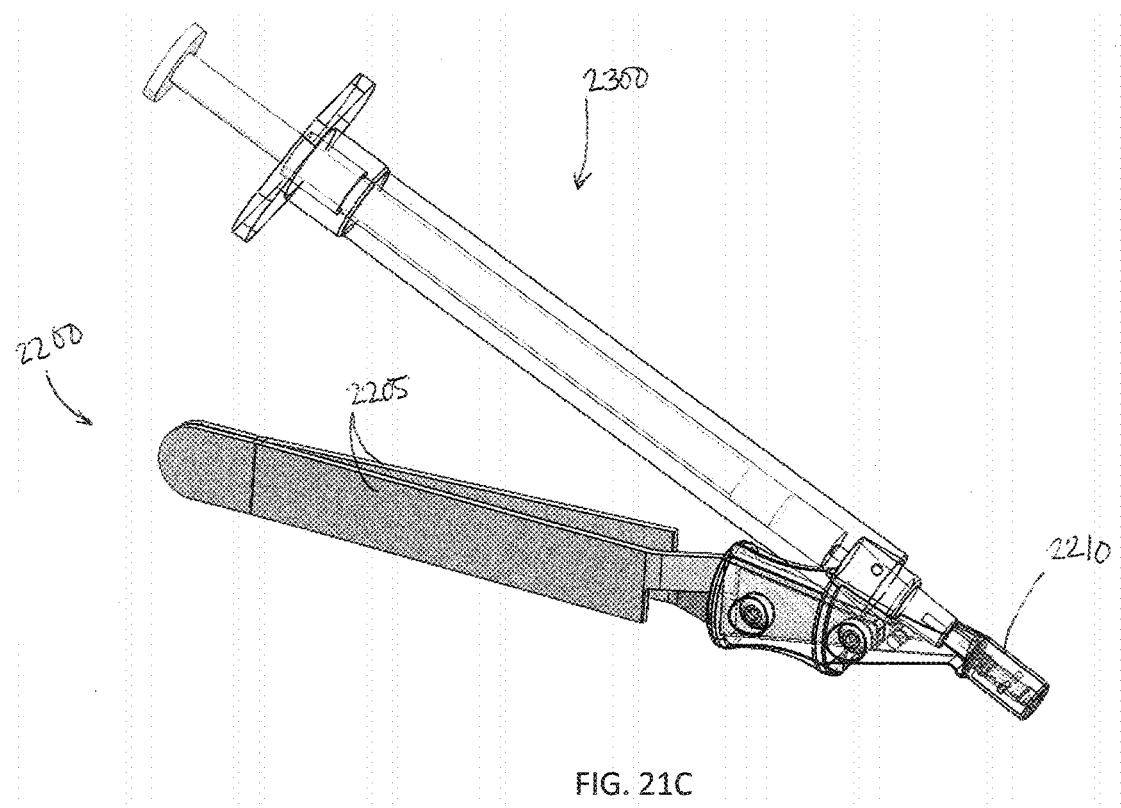
FIG. 21C is a perspective view of the priming tool of FIG. 21B holding the treatment device being primed with fluid.

The priming tool 2200 can further include a channel 2220 between the clamshells 2210 (see FIG. 21B) such that an upper surface of the treatment device 2100 can be accessed when the treatment device 2100 is held within the priming tool 2200. For example, the channel 2220 allows for insertion of a needle through the septum of the treatment device 2100 to prime and/or fill the device prior to insertion into a patient as shown in FIG. 21C. The channel 2220 of the priming tool 2200 can incorporate one or more features that provide proper alignment and access between the needle and the septum of the treatment device.

The treatment device 2100 can be primed using a priming needle. The priming needle can be part of an insertion tool or can be a separate priming needle of a separate tool. The priming needle can penetrate the septum of the treatment device 2100 constrained within the cavity 2215 between the opposing clamshells 2210 of the priming tool 2200. The priming needle can be coupled to a syringe filled with an amount of priming fluid. The syringe can be actuated such as via a plunger to inject fluid into the constrained device to purge air out of the device 2100. The air can be purged through a porous structure in the treatment device 2100, such as the drug release mechanism at a distal end of the treatment device 210, as the injected priming fluid is injected into the reservoir 2130 of the device 2100. The priming fluid can be a fluid such as saline or can be a drug solution to be delivered to the patient. Because the treatment device 2100 is constrained between the clamshells 2210 priming does not discernibly expand the reservoir 2130.

Figure 21D:
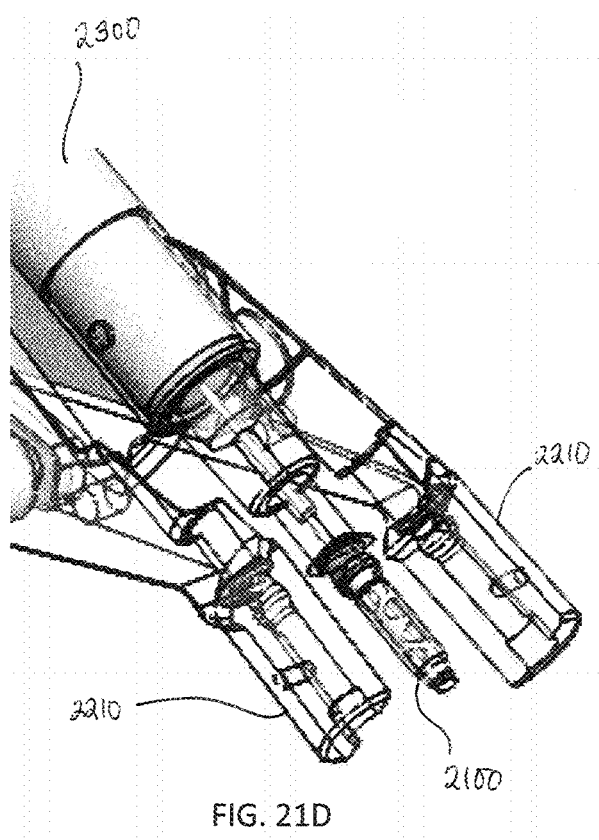
FIG. 21D is a detailed view of a distal end of a priming tool releasing a primed treatment device.
Figures 22A, 22B:
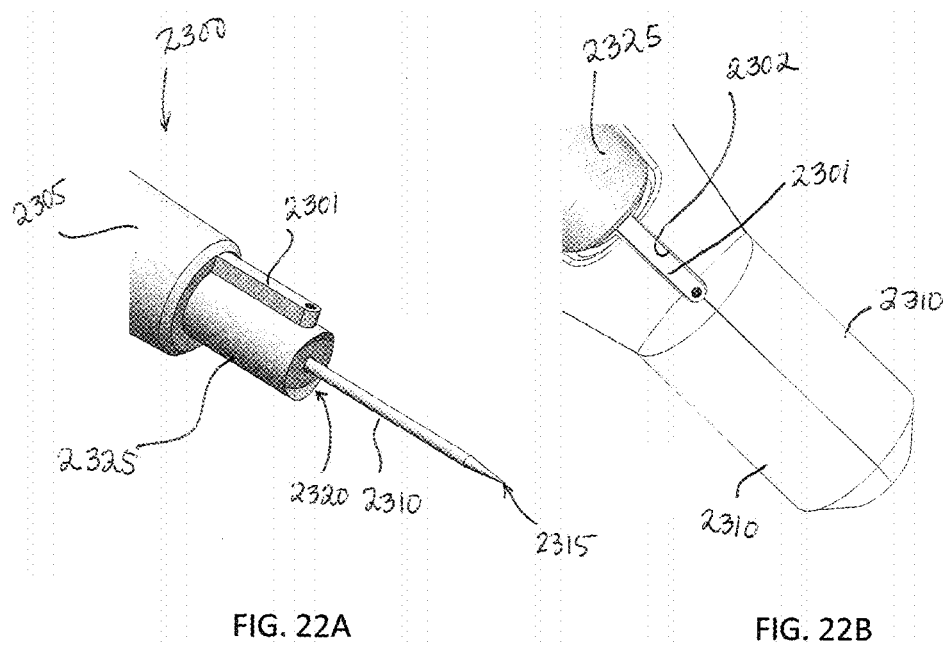
FIG. 22A illustrates a distal end of an implementation of an insertion tool.
FIG. 22B illustrates the insertion tool of FIG. 22A coupled with a priming tool.
Figures 23A, 23B:
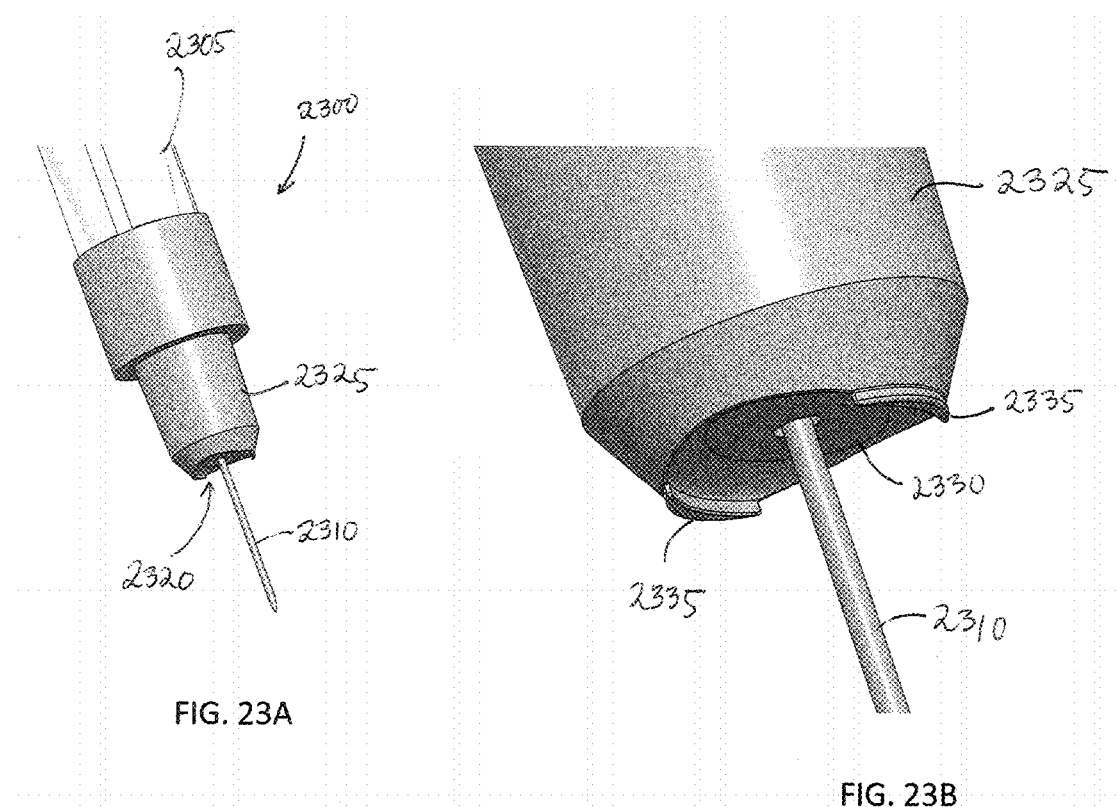
FIGS. 23A-23B are detailed views of a distal end region of an implementation of an insertion tool.

FIGS. 22A-22B shows an implementation of an insertion tool 2300 for use with the priming tool 2200. It should be appreciated that although the insertion tool 2300 is described as being separate from the priming tool 2200 and/or the priming needle, the various tools can be integrated within a single device or system that serves the various functions of holding, priming, and inserting. The insertion tool 2300 can include a proximal handle 2305 and a distal needle post 2310 having a pointed tip 2315, and optionally a seating element 2325 positioned between the needle post 2310 and the handle 2305. The needle post 2310 can be inserted through channel 2220 of the priming tool 220 and directed toward an upper surface of the treatment device 2100 held between the clamshells 2210. The needle post 2310 can penetrate through the septum of the treatment device 2100 held within the clamshells 2210 such that the device 2100 is secured to the insertion tool 2300. Once the treatment device 2100 is primed and secured to the insertion tool 2300, the priming tool 2200 can be actuated to move the clamshells 2210 away from one another releasing the treatment device 2100 from within the cavity 2215 therebetween (see FIG. 21D).

Again with respect to FIG. 22A-22B, the insertion tool 2300 can incorporate one or more body geometries, visual indicators, and/or mechanical keying features that allow for proper alignment upon insertion of the needle post 2310 through the septum of the treatment device 2100 held within the priming tool 2200. For example, a portion of the insertion tool 2300 can include a raised, mechanical key 2301 that extends outward from a cylindrical surface of the tool. The key 2301 can slide into a correspondingly shaped slot 2302 in a portion of the priming tool 2200. The key 2301 slides through the slot 2302 as the needle penetrates the septum only when the insertion tool 2300 is in a certain orientation relative to the priming tool 2200. The key 2301 prevents the needle from penetrating the septum in any other orientation as the key 2301 would abut the priming tool 2200 as the needle post 2310 inserts through the channel 2220. The insertion tool 2300 can also incorporate one or more visual markers to guide a user to position the insertion tool 2300 relative to the treatment device 2100 in a desired or known orientation. As such, once the treatment device 2100 is penetrated by the insertion tool 2300 the operator can be made generally aware of the relative orientation of the treatment device 2100 being held by the insertion tool 2300 and will know in which direction the eccentric volume of the reservoir 2130 will expand and can insert the treatment device 2100 through the incision accordingly.

Although the treatment device 2100 held by the insertion tool 2300 can be inserted through a puncture or an incision in the target region in a known manner, the orientation of the treatment device 2100 can be rotationally adjusted once inserted, if desired. In some implementations, the insertion tool 2300 can incorporate one or more features designed specifically to rotate the treatment device 2100 around the axis of insertion A. As mentioned above, the insertion tool 2300 can include a seating element 2325 configured to urge the treatment device 2100 through the incision. The seating element 2325 can have a distal end 2320 shaped to mate with and apply torque to the treatment device 2100. As best shown in FIGS. 23A-23E, the distal end 2320 of the seating element 2325 can include a cavity 2330 sized and shaped to receive at least a portion of the flange element 2110 at a proximal end of the treatment device 2100. As described elsewhere herein, the proximal flange element 2110 of the treatment device 2100 can have a specific geometry, for example a long axis and a short axis or an asymmetrical shape. The distal end 2320 of the insertion tool 2300 can slide down over the flange element 2110 such that the flange element 2110 inserts within the cavity 2330 such that the flange element 2110 and thus the treatment device 2100 rotates upon rotation of the insertion tool 2300. Additionally, the distal end 2320 can include a pair of edge features 2335 located on opposite sides of the cavity 2330 that can make contact with portions of the flange element 2110 to further aid in the rotation of the treatment device 2100 in a clockwise or counter-clockwise direction around the axis A. It should be appreciated that the seating element 2325 can also have a flat face at its distal-most end configured to abut an upper surface of the treatment device 2100 during insertion.

The seating element 2325 and/or the needle post 2310 can be movable relative to the handle 2305, for example, rotated as described above, advanced in a distal direction, and/or withdrawn in a proximal direction. Alternatively, the seating element 2325 and needle post 2310 can be fixed relative to the handle 2305 such that the entire insertion tool 2300 is moved by the operator in a clockwise, counter-clockwise, distal or proximal direction relative to a patient to seat the therapeutic device. Once the treatment device 2100 is properly oriented within the target treatment location, the seating element 2325 can be used to seat the treatment device 2100 into its final position in the incision with a single advancing motion.

FIGS. 24A-24F illustrate an implementation of an insertion tool 2300 having a handle 2305, a needle post 2310, a seating element 2325, an actuator 2345, and opposing end effectors 2350. The needle post 2310 and seating element 2325 can extend coaxially with each other as well as with the handle 2305 and the end effectors 2350. As described above, the treatment device 2100 can be held by the insertion tool 2300 such that the needle post 2310 extends through the septum of the device 2100. The needle post 2310 can be visible through an opening 2360 formed by the opposing end effectors 2350 (see FIG. 24D). The end effectors 2350 of the insertion tool 2300 can clamp onto the proximal end of the treatment device 2100. When the end effectors 2350 are closed around the flange element 2110 of the treatment device 2100, their distal ends 2355 wrap around a region of the treatment device 2100 near an underneath side of the flange element 2110. However, the thickness of these distal ends 2355 wrapping around the underneath side of the flange element 2110 fills this region of the treatment device 2100 that would otherwise be surrounded by the tissue through which the device 2100 is implanted if the device 2100 were fully seated within the incision. Thus, the end effectors 2350 can be urged away from one another (see FIG. 24E), for example by the sliding actuator 2345 as the device 2100 is seated in place. The seating element 2325 extending coaxially within the end effectors 2350 and over the needle post 2310 can be urged distally to press against the upper surface of the flange element 2110 of the treatment device 2100 (see FIG. 24F). The treatment device 2100 can thus be urged down into and seat within the incision. The movement of the seating element 2325 in a distal direction and the end effectors 2350 in outward direction can occur substantially simultaneously upon a single actuation of the actuator 2345 or in a step-wise manner such that the end effectors 2350 move away from the flange element 2110 before the seating element 2325 extends in a distal direction.

Figure 24A:
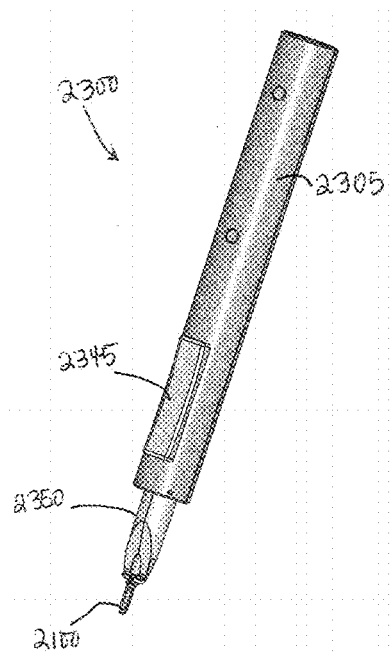
FIGS. 24A-24C illustrate an insertion tool coupled with a treatment device in various stages of implantation.
Figure 24B:
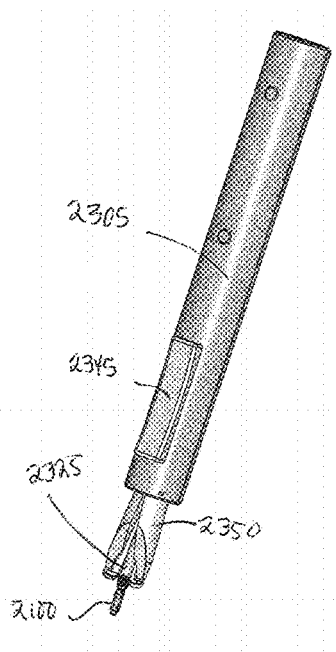
Figure 24C:
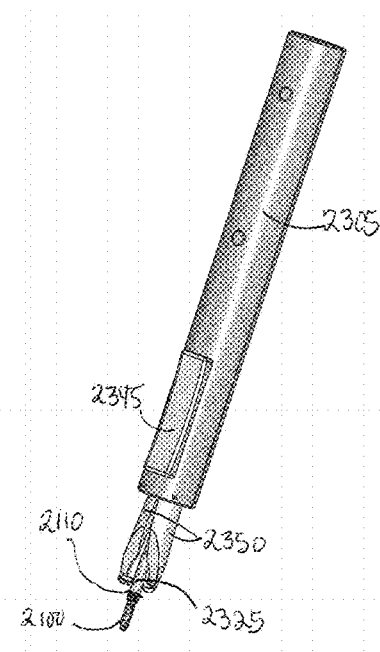
Figure 24D:
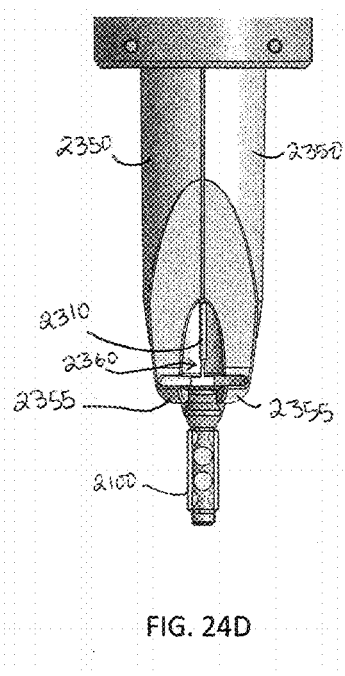
FIGS. 24D-24F are detailed views of the insertion tool of FIGS. 24A-24C in the various stages of implantation.
Figure 24E:
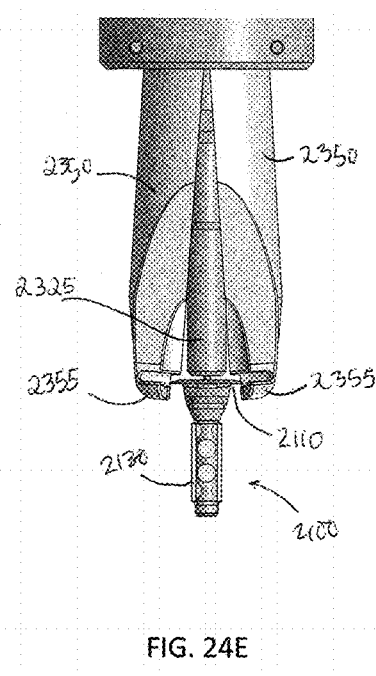
Figure 24F:
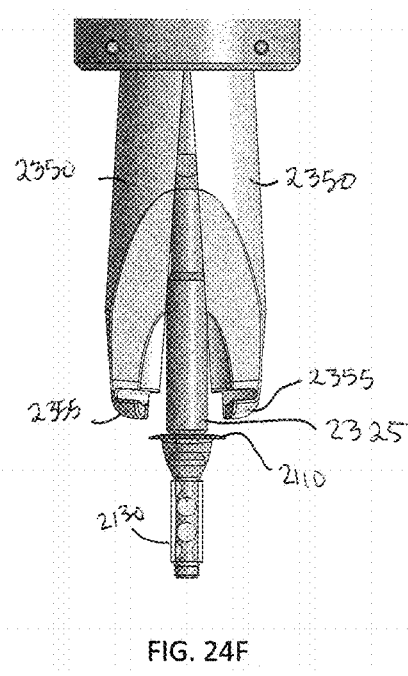
Figure 24G:
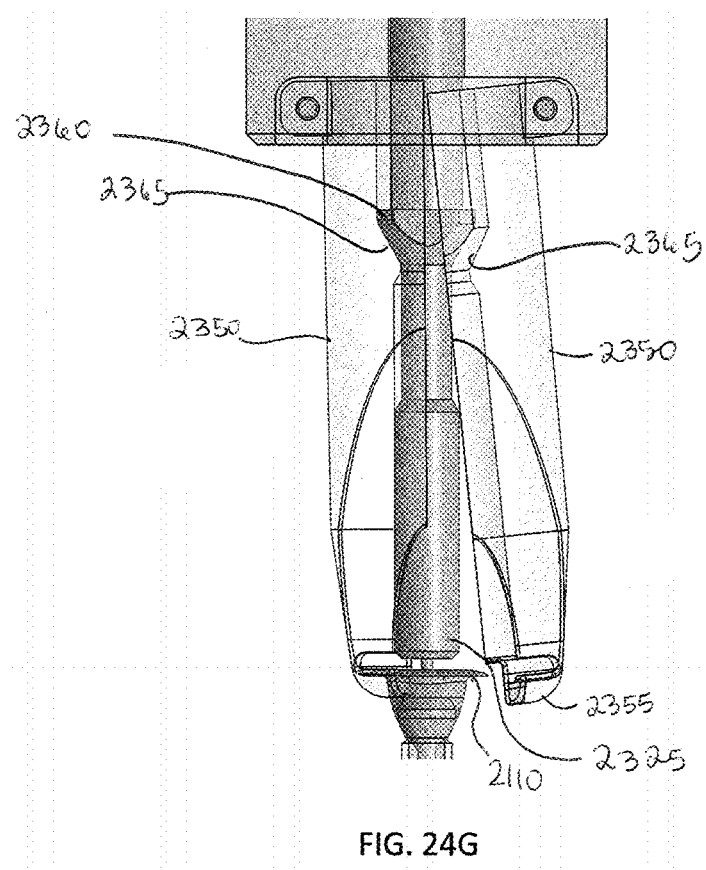
FIG. 24G is a detailed partially exploded, transparent view of the insertion tool of FIGS. 24D-24F.

In some implementations, the seating element 2325 can have an outer surface that is shaped to engage an inner surface of the end effectors 2350 to urge them in an outward direction as the seating element 2325 is advanced distally through the end effectors 2350 to seat the treatment device 2100. As best shown in FIG. 24G, the end effectors 2350 can be coupled at their proximal ends to the handle by a hinge pin such that the pair of end effectors 2350 can pivot towards and away from the axis A and each other. The seating element 2325 can extend distally between the end effectors 2350 coaxial to axis A within a central channel of the end effectors 2350. The central channel of the end effectors 2350 can include a feature 2365 such as a cam configured to engage a corresponding surface feature 2360 on an outer surface of the seating element 2325 extending through the central channel of the end effectors 2350. As such, when the seating element 2325 is urged in a forward, linear direction by the actuator 2345, the feature 2360 on the outer surface of the seating element 2325 engages the feature 2365 of the end effectors 2350 urging the end effectors 2350 to pivot outward away from one another. This releases the flange element 2110 of the treatment device 2100 being held by the distal ends of the end effectors 2350 such that the flange element 2110 can be seated within the incision in an unobstructed manner. The actuator 2345 can be coupled to the seating element 2325 by a retention spring that presses against the actuator 2345 and keeps the end effectors 2350 biased in a closed position around the treatment device 2100. The retention spring can also keep the needle post 2310 from puncturing the septum of the treatment device 2100 prior to implantation. Thus, this implementation of an insertion tool can hold the treatment device 2100 by the flange element 2110 by the distal ends of the end effectors 2350 and bias the needle post 2310 and the seating element 2325 in a proximal position until actuated to seat the device 2100.

The reservoir 2130 can be filled and expanded following implantation and seating of the device. However, it should be appreciated that the reservoir 2130 can be filled prior to, during, or after final seating the treatment device 2100 fully within the incision as will be described in more detail below.

Figure 25:
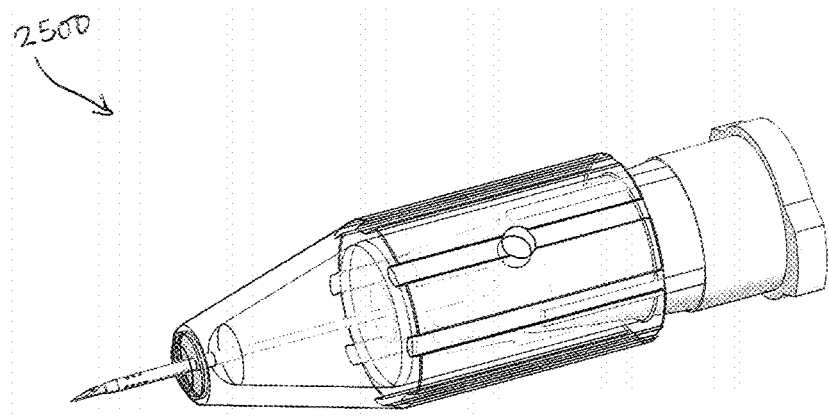
FIG. 25 is a perspective view of a refill needle and hub.

In some implementations, the fill needle 2500 can be a 30 gauge needle that has a hub providing visual feedback via its fluid return path when the treatment device 2100 has been filled (see FIG. 25). For example, the fill needle 2500 can include a transparent or translucent chamber for viewing return fluid. The fill needle 2500 can also include one or more return fluid path holes. The fill needle can be used to inject therapeutic fluid into the device 2100 until the prime fluid is removed from the treatment device 2100. The reservoir 2130 expands as the device 2100 is filled with fluid. The device 2100 can be slightly overfilled to ensure maximum expansion.

In some implementations, the fill needle 2500 can be the same as the prime needle used to prime and purge air from the treatment device as described above. The fill needle 2500 can also be the same as the needle on the insertion device 2300 used to hold and deliver the treatment device into position as described above. It should be appreciated that the priming needle, needle post 2310, and fill needle 2500 can each be separate devices such that three penetrations of the septum in the treatment device 2100 occurs during prime, insertion and filling. It should be appreciated that the priming needle, needle post 2310, and fill needle 2500 can be the same needle such that a single penetration of the septum is performed during prime, insertion and filling. Alternatively, the prime needle and needle post 2310 can be the same component and the fill needle 2500 separate component or the prime needle a separate component and the needle post 2310 and the fill needle 2500 the same component such that only two penetrations are needed to prime, insert, and fill the therapeutic device initially. It should also be appreciated that the treatment devices described herein can be refilled after a period of time. The septum of the treatment device can be penetrated during refill with a refill needle, for example such as that described in U.S. Pat. No. 9,033,911 or in U.S. Publication No. 2013/0165860, which are each incorporated by reference herein. The refill needle and the fill needle can be the same type of needle or can be distinct from one another. For example, the fill needle may or may not incorporate features to visualize filling whereas the refill needle does incorporate such features.

Once the expanded volume of the implanted reservoir is achieved, the device can be refilled at predictable intervals (e.g. every 3, 4, 5, 6 months or as along as every 12 months). However, changing the volume of the expanded device once implanted in the eye may not be desirable (e.g. movement in the eye once implanted may lead to potential trauma to surrounding structures or fluctuations in intraocular pressure) and is thus something to be avoided. The treatment devices described herein once implanted and expanded can maintain a consistent volume such that the outer diameter or contour of the reservoir does not change substantially throughout the use of the device and regardless of fill status. Further, the treatment devices described herein can maintain the same expanded shape even while fluid is being injected into the reservoir and/or while fluid is being removed from the reservoir (e.g. using the refill needle with or without flow directors). For example, drug passively diffuses through the porous drug delivery mechanism and out of the expanded reservoir over time. Despite this drug release into the eye, the expanded reservoir can remain filled with fluid, for example, fluid that enters the reservoir from the vitreous and drug formulation fluid remaining in the reservoir. The reservoir material can be formed of a substantially non-compliant material that tends to maintain its physical structure regardless of whether the interior of the reservoir is filled with drug. Further, refill of the treatment devices described herein can be performed such that a negative pressure and/or a positive pressure does not build within it. The refill and exchange devices used can incorporate features to avoid aspirating or evacuating the fluid within the reservoir and instead exchange the fluid while maintaining a substantially constant internal pressure. The treatment devices as well can incorporate one or more features to encourage this pressure-neutral exchange. For example, the treatment device can incorporate a central core element extending through the volume of the reservoir that has a wall surrounding a lumen, an inlet to the lumen, an outlet from the lumen, and one or more openings extending through the wall of the central core element between the inlet and the outlet. The lumen can be in fluid communication with the volume of the reservoir via the one or more openings. In some implementations, the one or more openings are located along the wall of the central core element to encourage exchange of new drug formulation fluid with the fluid remaining within the reservoir. For example, a first opening can be located near a distal end region of the central core element such that upon insertion of the refill/exchange needle through the inlet new drug formulation is delivered near this first opening. At least a second opening can be located near a proximal end region of the central core element. The fluid remaining within the reservoir that is to be exchanged for the new drug formulation can exit the reservoir volume through the second opening(s). An outlet lumen of the refill/exchange needle can be positioned near this second opening such that the fluid is removed from the treatment device through the outlet lumen. This arrangement of inlet and outlet openings in the central core element can encourage exchange of fluids (e.g. new formulation for old formulation) without mixing and without impacting the pressure within the reservoir volume that could impact the outer diameter or contour of the expandable reservoir. Further, the central core element can protect the material of the reservoir as the refill needle is inserted through the inlet of the central core element. The insertion configuration of the treatment device is when the non-compliant material of the reservoir is collapsed around the central core and forms a first three-dimensional shape prior to filling the volume with the one or more therapeutic agents. The non-compliant material of the reservoir is enlarged away from the central core element forming a second three-dimensional shape upon filling the volume with the one or more therapeutic agents when in an expanded configuration. This second three-dimensional shape achieved upon filling is then maintained throughout the life of the treatment device regardless of fill status or whether or not fluid is being added to the reservoir or taken from the reservoir.

The treatment devices described herein need not be removed and can remain in place indefinitely so long as therapeutically effective and beyond. However, the treatment device 2100 can be explanted (i.e. removed from the target location). Because the reservoir 2130 is expanded to a profile that is greater than the insertion profile, the reservoir 2130 is preferably unexpanded prior to removal. An aspiration needle can be connected, such as by tubing or other connector, to an aspiration device. The aspiration device can be a vacuum-lock syringe that creates a vacuum and provides suction for aspiration from the reservoir 2130. The syringe can be actuated by a luer lock lever, for example, to aspirate the reservoir 2130 of the treatment device 2100 and remove remaining contents. This system can be used to aspirate the contents of the reservoir 2130 for refill of the device and/or for removal of the device. The contents aspirated can be made visible through the aspiration device for visual feedback on completion of the aspiration process. Aspiration can collapse the expanded reservoir to a low profile such that the device 2100 can be explanted through the incision cavity. Smaller profile can reduce the removal force required as well as limit contact with internal tissues that can cause bleeding and damage. The aspirated and collapsed treatment devices described herein can be removed according to the methods and using the devices described in U.S. Patent Publication No. 2015/0080846, which is incorporated by reference herein. A long cannula or stylet can aid in stabilizing the therapeutic device during explanation, for example, if the device 2100 has no central core element 135, during evacuation of the reservoir 130 to a smaller outer diameter for ease of removal during explant.

Indications

The treatment devices described herein can be used to treat and/or prevent a variety of other ocular conditions besides glaucoma, including but not limited to dry or wet age-related macular degeneration (AMD), neuroprotection of retinal ganglion cells, cataract or presbyopia prevention, cancers, angiogenesis, neovascularization, choroidal neovascularization (CNV) lesions, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors such as neoplasms and retinoblastoma. Still further conditions that can be treated and/or prevented using the devices and methods described herein, include but are not limited to hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves' disease, systemic lupus erythematosus and rheumatoid arthritis, shock and wasting disorders, cystic fibrosis, lactose intolerance, Crohn's disease, inflammatory bowel disease, gastrointestinal or other cancers, degenerative diseases, trauma, multiple systemic conditions such as anemia.

Therapeutics

Examples of therapeutic agents that may be delivered by the treatment devices described herein and/or are described in the applications incorporated by reference herein are provided below and in Table 1, which is incorporated herein in its entirety.

Therapeutics that can be delivered from the devices described herein include but are not limited to Triamcinolone acetonide, Bimatoprost (Lumigan) or the free acid of bimatoprost, latanoprost or the free acid or salts of the free acid of latanoprost, Ranibizumab (Lucentis™) Travoprost (Travatan, Alcon) or the free acid or salts of the free acid of travoprost, Timolol (Timoptic, Merck), Levobunalol (Betagan, Allergan), Brimonidine (Alphagan, Allergan), Dorzolamide (Trusopt, Merck), Brinzolamide (Azopt, Alcon). Additional examples of therapeutic agents that may be delivered by the therapeutic device include antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluorometholone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors. Other therapeutic agents known to those skilled in the art which are capable of controlled, sustained release into the eye in the manner described herein are also suitable for use in accordance with embodiments of the devices described herein.

The therapeutic agent can also include one or more of the following: Abarelix, Abatacept, Abciximab, Adalimumab, Aldesleukin, Alefacept, Alemtuzumab, Alpha-1-proteinase inhibitor, Alteplase, Anakinra, Anistreplase, Antihemophilic Factor, Antithymocyte globulin, Aprotinin, Arcitumomab, Asparaginase, Basiliximab, Becaplermin, Bevacizumab, Bivalirudin, Botulinum Toxin Type A, Botulinum Toxin Type B, Capromab, Cetrorelix, Cetuximab, Choriogonadotropin alfa, Coagulation Factor IX, Coagulation factor VIIa, Collagenase, Corticotropin, Cosyntropin, Cyclosporine, Daclizumab, Darbepoetin alfa, Defibrotide, Denileukin diftitox, Desmopressin, Dornase Alfa, Drotrecogin alfa, Eculizumab, Efalizumab, Enfuvirtide, Epoetin alfa, Eptifibatide, Etanercept, Exenatide, Felypressin, Filgrastim, Follitropin beta, Galsulfase, Gemtuzumab ozogamicin, Glatiramer Acetate, Glucagon recombinant, Goserelin, Human Serum Albumin, Hyaluronidase, Ibritumomab, Idursulfase, Immune globulin, Infliximab, Insulin Glargine recombinant, Insulin Lyspro recombinant, Insulin recombinant, Insulin, porcine, Interferon Alfa-2a, Recombinant, Interferon Alfa-2b, Recombinant, Interferon alfacon-1, Interferonalfa-n1, Interferon alfa-n3, Interferon beta-1b, Interferon gamma-1b, Lepirudin, Leuprolide, Lutropin alfa, Mecasermin, Menotropins, Muromonab, Natalizumab, Nesiritide, Octreotide, Omalizumab, Oprelvekin, OspA lipoprotein, Oxytocin, Palifermin, Palivizumab, Panitumumab, Pegademase bovine, Pegaptanib, Pegaspargase, Pegfilgrastim, Peginterferon alfa-2a, Peginterferon alfa-2b, Pegvisomant, Pramlintide, Ranibizumab, Rasuricase, Reteplase, Rituximab, Salmon Calcitonin, Sargramostim, Secretin, Sermorelin, Serum albumin iodonated, Somatropin recombinant, Streptokinase, Tenecteplase, Teriparatide, Thyrotropin Alfa, Tositumomab, Trastuzumab, Urofollitropin, Urokinase, or Vasopressin.

The therapeutic agent can include one or more of compounds that act by binding members of the immunophilin family of cellular proteins. Such compounds are known as "immunophilin binding compounds" Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories). The limus family of compounds may be used in the compositions, devices and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD.

The therapeutic agent can include one or more of: pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including.gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

The therapeutic agent can include inhibitors of VEGF receptor kinase; inhibitors of VEGFA, VEGFC, VEGFD, bFGF, PDGF, Ang-2, PDGFR, cKIT, FGF, BDGF, mTOR, $\alpha v\beta 3$, $\alpha v\beta 5$, $\alpha 5\beta 1$ integrin, and alpha2 adrenergic receptor; inhibitors of complement factor B (e.g. TA106), complement factor D (CFD) (Lampalizumab/TNX-234), C3 (e.g. APL-2, novel compstatin analogs), C5 (e.g. Eculizumab, Zimura, ARC1905, ALN-CC5), C5a (e.g. JPE-1375), and tubulin; AAV-CD56 The therapeutic agent can also include Complement Factor H (CFH), engineered mini-CFH, or recombinant CFH (rCFH).

The therapeutic agent can include a combination with other therapeutic agents and therapies, including but not limited to agents and therapies useful for the treatment of angiogenesis or neovascularization, particularly CNV. Non-limiting examples of such additional agents and therapies include pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibizumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

Prostaglandin analogues (PGAs) can be used to increase outflow of aqueous through the ciliary body and/or the trabecular meshwork including travaprost (0.004%), bimatoprost (0.03%, 0.01%), tafluprost (0.0015%), and latanoprost (0.005%). Beta blockers can be used to reduce aqueous fluid production by the ciliary body. Drugs in this class include timolol (0.5%). Carbonic anhydrase inhibitors can be used to reduce aqueous fluid production by the ciliary body as well. Drugs in this class include brinzolamide (1%), methazolamide, dorzolamide (2%), and acetazolamide. Alpha antagonists can be used to reduce aqueous fluid production by the ciliary body and increase outflow through the trabecular meshwork. Thus, the drug targets tissues located in both the anterior chamber and the posterior chamber and as such the devices can be implanted in either location to achieve a therapeutic result. Drugs in this class include brimonidine (0.1%, 0.15%) and apraclonidine (0.5%, 1.0%). Commercially available combinations of therapeutics considered herein include COMBIGAN® (brimonidine tartrate/timolol maleate ophthalmic solution; Allergan), and COSOPT® (dorzolamide hydrochloride-timolol maleate ophthalmic solution; Merck). Further, other sustained release therapeutics considered herein include subconjunctival latanoprost (Psivida/Pfizer), intracameral bimatoprost (Allergan), and intravitreal brimonidine (Allergan).

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, polyoxyethylene stearate and the like. The carrier may also contain adjuvants such as preserving, stabilizing, wetting, emulsifying agents or other related materials Materials Generally, the components of the devices described herein are fabricated of materials that are biocompatible and preferably insoluble in the body fluids and tissues that the device comes into contact with. The materials generally do not cause irritation to the portion of the eye that it contacts. Materials may include, by way of example, various polymers including, for example, silicone elastomers and rubbers, polyolefins, polyurethanes, acrylates, polycarbonates, polyamides, polyimides, polyesters, and polysulfones. One or more components of the devices described herein can be fabricated of a permeable material including, but not limited to, polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers and porous rubbers. One or more components of the devices described herein can be fabricated of a nonbiodegradable polymer, including but not limited to polymethylmethacrylate, a silicone elastomer, or silicone rubber. Other suitable non-erodible, biocompatible polymers which may be used in fabricating the devices described herein may include polyolefins such as polypropylene and polyethylene, homopolymers, and copolymers of vinyl acetate such as ethylene vinyl acetate copolymer, polyvinylchlorides, homopolymers and copolymers of acrylates such as polyethylmethacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, natural rubber, polyisobutylene, polymethylstyrene and other similar non-erodible biocompatible polymers.

One or more of the components of the devices described herein can be fabricated of a substantially non-compliant material that can be expanded to a particular shape. One or more of the components of the devices described herein can be fabricated of a rigid, non-pliable material. One or more of the components of the devices described herein can be fabricated of a shape memory material and/or superelastic material including, but not limited to shape memory alloys (SMA) like Nitinol (Ni—Ti alloy) and shape memory polymers (SMP) like AB-polymer networks based on oligo(e-caprolactone) dimethacrylates and n-butyl acrylate. Shape memory alloys generally have at least two phases: (1) a martensite phase, which has a relatively low tensile strength and which is stable at relatively low temperatures, and (2) an austenite phase, which has a relatively high tensile strength and which is stable at temperatures higher than the martensite phase. The shape memory characteristics are imparted on the material by heating the material to a temperature above the temperature at which the austenite phase is stable. While the material is heated to this temperature, the device is held in the "memory shape", which is shape that is desired to be "remembered".

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed. The claimed subject matter has been described in conjunction with the detailed description thereof, the foregoing description is intended to illustrate and not limit the scope of the claimed subject matter of the appended claims.

TABLE 1

Therapeutic Agent List

| Generic Name | Brands (Companies) | Category | Indication | Molecular Weight |
|---|---|---|---|---|
| 2-Methoxyestradiol analogs 3-aminothalidomide | (Paloma Pharmaceuticals) | Angiogenesis inhibitors | AMD | |
| 13-cis retinoic acid | Accutane TM (Roche Pharmaceuticals) | | | |
| A0003 | (Aqumen BioPharmaceuticals) | A0003 | AMD | |
| A5b1 integrin inhibitor | (Jerini Ophthalmic); (Ophthotech) | Inhibitors of a5b1 integrin | AMD | |
| Abarelix | Plenaxis ™ (Praecis Pharmaceuticals) | Anti-Testosterone Agents; Antineoplastic Agents | For palliative treatment of advanced prostate cancer. | 37731 |
| Abatacept | Orencia ™ (Bristol-Myers Squibb) | Antirheumatic Agents | For the second line reduction of the signs and symptoms of moderate-to-severe active rheumatoid arthritis, inducing major clinical response, slowing the progression of structural damage, and improving physical function in adult patients who have | 37697 |
| Abciximab | ReoPro ™; ReoPro ™ (Centocor) | Anticoagulants; Antiplatelet Agents | For treatment of myocardial infarction, adjunct to percutaneous 49oronary intervention, unstable angina | 42632 |
| ABT-578 | (Abbott Laboratories) | Limus Immunophilin Binding Compounds | | |
| Acetonide Adalimumab | Humira ™ (Abbott Laboratories) | Antirheumatic Agents; Immunomodulatory Agents | Uveitis, AMD | 25645 |

TABLE 1-continued

Therapeutic Agent List

| Generic Name | Brands (Companies) | Category | Indication | Molecular Weight |
|---|---|---|---|---|
| Aldesleukin | Proleukin ™; Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |
| Alteplase | Activase ™ (Genentech Inc) | Thrombolytic Agents | For management of acute myocardial infarction, acute ischemic stroke and for lysis of acute pulmonary emboli | 54732 |
| AMG-1470 | | | | |
| Anakinra | Kineret ™ (Amgen Inc) | Anti-Inflammatory Agents, Non-Steroidal; Antirheumatic Agents; Immunomodulatory Agents | For the treatment of adult rheumatoid arthritis. | 65403 |
| Anecortave acetate | | | | |
| Angiostatin | | | | |
| Anistreplase | Eminase ™ (Wulfing Pharma GmbH) | Thrombolytic Agents | For lysis of acute pulmonary emboli, intracoronary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |
| Anti-angiogeric bifunctional protein | Icon-1 ™ (Iconic Therapeutics) | Anti-angiogeric bifunctional protein, Icon-1 | AMD | |
| Anti-endothelial growth factor | | | | |
| Antihemophilic Factor | Advate ™; Alphanate ™; Bioclate ™; Helixate ™; Helixate FS ™; Hemofil M ™; Humate-P ™; Hyate:C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand disease and Factor XIII deficiency | 70037 |
| Antithymocyte globulin | Genzyme); Thymoglobulin ™ (SangStat Medical | Immunomodulatory Agents | For prevention of renal transplant rejection | 37173 |
| Anti-hypertensive MC1101 | (MacuCLEAR) | Anti-hypertensive MC1101 | AMD | |
| Anti-platelet derived growth factor | | | | |
| Anti-VEGF | (Neurotech); Avastin ™ (NeoVista) | Anti-VEGF | AMD | |
| AP23841 | (Ariad) | Limus Immunophilin Binding Compounds | | |

TABLE 1-continued

Therapeutic Agent List

| Generic Name | Brands (Companies) | Category | Indication | Molecular Weight |
|---|---|---|---|---|
| ARC1905 | Ophthotech | Complement Cascade Inhibitor (Factor C5) | | |
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who are at an increased risk for blood loss and blood transfusion | 90569 |
| Arcitumomab | CEA-Scan ™ | Diagnostic Agents; Imaging Agents | For imaging colorectal tumors | 57561 |
| Asparaginase | Elspar ™ (Merck & Co. Inc) | Antineoplastic Agents | For treatment of acute lympocytic leukemia and non-Hodgkins lymphoma | 132.118 |
| Axitinib | | Tyrosine Kinase Inhibitors | | 386 |
| Basiliximab | Simulect ™ (Novartis Pharmaceuticals) | Immunomodulatory Agents; Immunosuppressive Agents | For prophylactic treatment of kidney transplant rejection | 61118 |
| Becaplermin | Regranex ™; Regranex ™ (OMJ Pharmaceuticals) | Anti-Ulcer Agents; Topical | For topical treatment of skin ulcers (from diabetes) | 123969 |
| Bevacizumab | Avastin ™; Avastin ™ (Genentech Inc) | Antiangiogenesis Agents; Antineoplastic Agents | For treatment of metastatic colorectal cancer | 27043 |
| Bivalirudin | Angiomax ™; Angiomax ™ (Medicines Co or MDCO); Angiox ™ | Anticoagulants; Antithrombotic Agents | For treatment of heparin-induced thrombocytopenia | 70037 |
| Bortezomib | | Proteosome Inhibitors | | |
| Bosutinib | | Tyrosine Kinase Inhibitors | | 530 |
| Botulinum Toxin Type A | BOTOX ™ (Allegran Inc); BOTOX Cosmetic ™ (Allegran Inc); Botox ™; Dysport ™ | Anti-Wrinkle Agents; Antidystonic Agents; Neuromuscular Blocking Agents | For the treatment of cervical dystonia in adults to decrease the severity of abnormal head position and neck pain associated with cervical dystonia. Also for the treatment of severe primary axillary hyperhidrosis that is inadequately managed with topical | 23315 |
| Botulinum Toxin Type B | Myobloc ™ (Solstice Neurosciences); Neurobloc ™ (Solstice Neurosciences) | Antidystonic Agents | For the treatment of patients with cervical dystonia to reduce the severity of abnormal head position and neck pain associated with cervical dystonia. | 12902 |
| C5 inhibitor | (Jerini Ophthalmic); (Ophthotech) | Inhibitors of C5 | AMD | |
| Cal101 | Calistoga | PI3Kdelta Inhibitor | AMD, DME | |
| Canstatin | | | | |
| Capromab | ProstaScint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |

TABLE 1-continued

Therapeutic Agent List

| Generic Name | Brands (Companies) | Category | Indication | Molecular Weight |
|---|---|---|---|---|
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™; Erbitux ™ (ImClone Systems Inc) | Antineoplastic Agents | For treatment of metastatic colorectal cancer. | 42632 |
| Choriogonadotropin alfa | Novarel ™; Ovidrel ™; Pregnyl ™; Profasi ™ | Fertility Agents; Gonadotropins | For the treatment of female infertility | 78617 |
| Cilary neurotrophic factor | (Neurotech) | Cilary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | NovoSeven ™ (Novo Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ | Anti-Ulcer Agents; Topical | For treatment of chronic dermal ulcers and severe skin burns | 138885 |
| Complement factor H recombinant | (Optherion); (Taligen Therapeutics) | Complement factor H recombinant | AMD, Geographic Atrophy | |
| Compstatin derivative peptide, POT-4 | (Potentia Pharmaceuticals) | Complement Factor C3 Inhibitors; Compstatin Derivative Peptides | AMD | |
| Corticotropin | ACTH ™; Acethropan ™; Acortan ™; Acthar ™; Exacthin ™; H.P. Acthar Gel ™; Isactid ™; Purified cortrophin gel ™; Reacthin ™; Solacthyl ™; Tubex | Diagnostic Agents | For use as a diagnostic agent in the screening of patients presumed to have adrenocortical insufficiency. | 33927 |
| Cosyntropin | Cortrosyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |
| Cyclosporine | Gengraf ™ (Abbott labs); Neoral ™ (Novartis); Restasis ™; Restasis ™ (Allergan Inc); Sandimmune ™ (Novartis); Sangcya ™ | Antifungal Agents; Antirheumatic Agents; Dermatologic Agents; Enzyme Inhibitors; Immunomodulatory Agents; Immunosuppressive Agents | For treatment of transplant rejection, rheumatoid arthritis, severe psoriasis | 32953 |
| Daclizumab | Zenapax ™ (Hoffmann-La Roche Inc) | Immunomodulatory Agents; Immunosuppressive Agents | For prevention of renal transplant rejection; Uveitis | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |

TABLE 1-continued

Therapeutic Agent List

| Generic Name | Brands (Companies) | Category | Indication | Molecular Weight |
|---|---|---|---|---|
| Defibrotide | Dasovas ™; Noravid ™; Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatics; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflammation, macular edema following branch retinal vein occlusion (BRVO) or central retinal vein occlusion (CRVO) | 392 |
| Diclofenac | | Cyclooxygenase Inhibitors | | |
| Dithiocarbamate | | NFκB Inhibitor | | |
| Dornase Alfa | Dilor ™; Dilor-400 ™; Lufyllin ™; Lufyllin-400 ™; Neothylline ™; Pulmozyme ™ (Genentech Inc) | Enzyme Replacement Agents | For the treatment of cystic fibrosis. | 7656 (double strand) |
| Drotrecogin alfa | Xigris ™; Xigris ™ (Eli Lilly & Co) | Antisepsis Agents | For treatment of severe sepsis | 267012 |
| Eculizumab | Soliris ™; Soliris ™ (Alexion Pharmaceuticals) | Complement Cascade Inhibitor (Factor C5) | AMD | 188333 |
| Efalizumab | Raptiva ™; Raptiva ™ (Genentech Inc) | Immunomodulatory Agents; Immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epomax ™ (Elanex); Eprex ™ (Janssen-Cilag. Ortho Biologics LLC); NeoRecormon ™ (Roche); Procrit ™ (Ortho Biotech); Recormon ™ (Roche) | Antianemic Agents | For treatment of anemia (from renal transplants or certain HIV treatment) | 55066 |

TABLE 1-continued

Therapeutic Agent List

| Generic Name | Brands (Companies) | Category | Indication | Molecular Weight |
|---|---|---|---|---|
| Eptifibatide | Integrilin ™; Integrilin ™ (Millennium Pharm) | Anticoagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Antirheumatic Agents; Immunomodulatory Agents | Uveitis, AMD | 25645 |
| Everolimus | Novartis | Limus Immunophilin Binding Compounds, mTOR | AMD | |
| Exenatide | Byetta ™; Byetta ™ (Amylin/Eli Lilly) | | Indicated as adjunctive therapy to improve glycemic control in patients with Type 2 diabetes mellitus who are taking metformin, a sulfonylurea, or a combination of both, but have not achieved adequate glycemic control. | 53060 |
| FCFD4514S | Genentech/Roche | Complement Cascade Inhibitor (Factor D) | AMD, Geographic Atrophy | |
| Felypressin | Felipresina ™ [INN-Spanish]; Felipressina ™ [DCIT]; Felypressin ™ [USAN:BAN:INN]; Felypressine ™ [INN-French]; Felypressinum ™ [INN-Latin]; Octapressin ™ | Renal Agents; Vasoconstrictor Agents | For use as an alternative to adrenaline as a 56ocalizing agent, provided that local ischaemia is not essential. | 46800 |
| Fenretinide | Sirion/reVision Therapeutics | Binding Protein Antagonist for Oral Vitamin A | AMD, Geographic Atrophy | |
| Filgrastim | Neupogen ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| FK605-binding proteins, FKBPs | | Limus Immunophilin Binding Compounds | | |
| Fluocinolone Acetonide | Retisert ™ (Bausch & Lomb); Iluvien ™ (Alimera Sciences, Inc.) | Glucocorticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Naglazyme ™; Naglazyme ™ (BioMarin Pharmaceuticals) | Enzyme Replacement Agents | For the treatment of adults and children with Mucopolysaccharidosis VI. | 47047 |
| Gefitinib | | Tyrosine Kinase Inhibitors | | 447 |
| Gemtuzumab ozogamicin | Mylotarg ™; Mylotarg ™ (Wyeth) | Antineoplastic Agents | For treatment of acute myeloid leukemia | 39826 |
| Glatiramer Acetate | Copaxone ™ | Adjuvants, Immunologic; Immunosuppressive Agents | For reduction of the frequency of relapses in patients with Relapsing-Remitting Multiple Sclerosis. | 29914 |

TABLE 1-continued

Therapeutic Agent List

| Generic Name | Brands (Companies) | Category | Indication | Molecular Weight |
|---|---|---|---|---|
| Glucagon recombinant | GlucaGen ™ (Novo Nordisk); Glucagon ™ (Eli Lilly) | Antihypoglycemic Agents | For treatment of severe hypoglycemia, also used in gastrointestinal imaging | 54009 |
| Goserelin | Zoladex ™ | Antineoplastic Agents; Antineoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |
| Hyaluronidase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Elaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | AMD, DME | 494 |
| Immune globulin | Civacir ™; Flebogamma ™ (Instituto Grifols SA); Gamunex ™ (Talecris Biotherapeutics) | Anti-Infectives; Immunomodulatory Agents | For treatment of immunodeficiencies, thrombocytopenic purpura, Kawasaki disease, gammablobulinemia, leukemia, bone transplant | 42632 |
| Infliximab | Remicade ™ (Centocor Inc) | Immunomodulatory Agents; Immunosuppressive Agents | Uveitis, AMD | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lily); Insulin Lispro (Eli Lily) | Hypoglycemic Agents | For treatment of diabetes (type I and II) | 154795 |
| Insulin recombinant | Novolin R ™ (Novo Nordisk) | Hypoglycemic Agents | For treatment of diabetes (type I and II) | 156308 |
| Insulin, porcine | Iletin II ™ | Hypoglycemic Agents | For the treatment of diabetes (type I and II) | 156308 |
| Interferon Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papiloma Virus | 57759 |

TABLE 1-continued

Therapeutic Agent List

| Generic Name | Brands (Companies) | Category | Indication | Molecular Weight |
|---|---|---|---|---|
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata 59cuminate. | 57759 |
| Interferon beta-1b | Betaseron ™ (Chiron Corp) | Antiviral Agents; Immunomodulatory Agents | For treatment of relapsing/remitting multiple sclerosis | 57759 |
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |
| Mecasermin | Increlex ™; Increlex ™ (Tercica); Iplex | | For the long-term treatment of growth failure in pediatric patients with Primary IGFD or with GH gene deletion who have developed neutralizing antibodies to GH. It is not indicated to treat Secondary IGFD resulting from GH deficiency, malnutrition, hypoth | 154795 |
| Menotropins | Repronex ™ | Fertility Agents | For treatment of female infertility | 78617 |
| Methotrexate | | Immunomodulatory | Uveitis, DME | |
| mTOR inhibitors | | | | |
| Muromonab | Orthoclone OKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™; Longastatin ™; Sandostatin ™; Sandostatin LAR ™; Sandostatin LAR ™ (Novartis) | Anabolic Agents; Antineoplastic Agents, Hormonal; Gastrointestinal Agents; Hormone Replacement Agents | For treatment of acromegaly and reduction of side effects from cancer chemotherapy | 42687 |
| Omalizumab | Xolair ™ (Genentech Inc) | Anti-Asthmatic Agents; Immunomodulatory Agents | For treatment of asthma caused by allergies | 29596 |

TABLE 1-continued

Therapeutic Agent List

| Generic Name | Brands (Companies) | Category | Indication | Molecular Weight |
|---|---|---|---|---|
| Oprelvekin | Neumega ™; Neumega ™ (Genetics Institute Inc) | Coagulants; Thrombotics | Increases reduced platelet levels due to chemotherapy | 45223 |
| OspA lipoprotein | LYMErix ™ (SmithKline Beecham) | Vaccines | For prophylactic treatment of Lyme Disease | 95348 |
| OT-551 | (Othera) | Anti-oxidant eyedrop | AMD | |
| Oxytocin | Oxytocin ™ (BAM Biotech); Pitocin ™ (Parke-Davis); Syntocinon ™ (Sandoz) | Anti-tocolytic Agents; Labor Induction Agents; Oxytocics | To assist in labor, elective labor induction, uterine contraction induction | 12722 |
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases caused by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatin-, and irinotecan-containing chemotherapy regimens. | 134279 |
| PDGF inhibitor | (Jerini Ophthalmic); (Ophthotech) | Inhibitors of PDGF | AMD | |
| PEDF (pigment epithelium derived factor) | | | | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |
| Pegaspargase | Oncaspar ™ (Enzon Inc) | Antineoplastic Agents | For treatment of acute lymphoblastic leukemia | 132.118 |
| Pegfilgrastim | Neulasta ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Schering Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |

TABLE 1-continued

Therapeutic Agent List

| Generic Name | Brands (Companies) | Category | Indication | Molecular Weight |
|---|---|---|---|---|
| Pegvisomant | Somavert ™ (Pfizer Inc) | Anabolic Agents; Hormone Replacement Agents | For treatment of acromegaly | 71500 |
| Pentoxifylline | | | | |
| Perindozril | | ACE Inhibitors | | |
| Pimecrolimus | | Limus Immunophilin Binding Compounds | | |
| PKC (protein kinase C) inhibitors | | | | |
| POT-4 | Potentia/Alcon | Complement Cascade Inhibitor (Factor C3) | AMD | |
| Pramlintide | Symlin ™; Symlin ™ (Amylin Pharmaceuticals) | | For the mealtime treatment of Type I and Type II diabetes in combination with standard insulin therapy, in patients who have failed to achieve adequate glucose control on insulin monotherapy. | 16988 |
| Proteosome inhibitors | Velcade ™ | | Proteosome inhibitors | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (siroliums) | (MacuSight) | Limus Immunophilin Binding Compounds | AMD | |
| Rasburicase | Elitek ™; Elitek ™ (Sanofi-Synthelabo Inc); Fasturtec ™ | Antihyperuricemic Agents | For treatment of hyperuricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |
| Retinal stimulant | Neurosolve ™ (Vitreoretinal Technologies) | Retinal stimulants | AMD | |
| Retinoid(s) | | | | |
| Rituximab | MabThera ™; Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™; Miacalcin ™ (Novartis) | Antihypocalcemic Agents; Antiosteporotic Agents; Bone Density Conservation Agents | For the treatment of post-menopausal osteoporosis | 57304 |

TABLE 1-continued

Therapeutic Agent List

| Generic Name | Brands (Companies) | Category | Indication | Molecular Weight |
|---|---|---|---|---|
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SAR 1118 | SARCode | Immunomodulatory Agent | Dry eye, DME, conjunctivitis | |
| SDZ-RAD | | Limus Immunophilin Binding Compounds | | |
| Secretin | SecreFlo ™; Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| SF1126 | Semafore | Pl3k/mTOR Inhibition | AMD, DME | |
| Sirolimus reformulation (rapamycin) | (MacuSight) | Limus Immunophilin Binding Compounds | AMD | |
| siRNA molecule synthetic, FTP-801i-14 | (Quark Pharmaceuticals) | siRNA molecule synthetic | AMD | |
| Somatropin recombinant | BioTropin ™ (Biotech General); Genotropin ™ (Pfizer); Humatrope ™ (Eli Lilly); Norditropin ™ (Novo Nordisk); Nutropin ™ (Genentech Inc.); NutropinAQ ™ (Genentech Inc.); Protropin ™ (Genentech Inc.); Saizen ™ (Serono SA); Serostim ™; Serostim ™ (Serono SA); Tev-Tropin ™ (GATE) | Anabolic Agents; Hormone Replacement Agents | For treatment of dwarfism, acromegaly and prevention of HIV-induced weight loss | 71500 |
| Squalamine | | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| TA106 | Taligen | Complement Cascade Inhibitor (Factor B) | AMD | |

TABLE 1-continued

Therapeutic Agent List

| Generic Name | Brands (Companies) | Category | Indication | Molecular Weight |
|---|---|---|---|---|
| Tacrolimus | | Limus Immunophilin Binding Compounds | | |
| Tenecteplase | TNKase ™ (Genentech Inc) | Thrombolytic Agents | For treatment of myocardial infarction and lysis of intracoronary emboli | 54732 |
| Teriparatide | Apthela ™; Forsteo ™; Forteo ™; Fortessa ™; Opthia ™; Optia ™; Optiah ™; Zalectra ™; Zelletra ™ | Bone Density Conservation Agents | For the treatment of osteoporosis in men and postmenopausal women who are at high risk for having a fracture. Also used to increase bone mass in men with primary or hypogonadal osteoporosis who are at high risk for fracture. | 66361 |
| Tetrathiomolybdate | | | | |
| Thalidomide | Celgene | Anti-inflammatory, Anti-proliferative | Uveitis | |
| Thyrotropin Alfa | Thyrogen ™ (Genzyme Inc) | Diagnostic Agents | For detection of residual or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxar ™ (Corixa Corp) | Antineoplastic Agents | For treatment of non-Hodgkin's lymphoma (CD20 positive, follicular) | 33078 |
| TPN 470 analogue | | | | |
| Trastuzumab | Herceptin ™ (Genentech) | Antineoplastic Agents | For treatment of HER2-positive pulmonary breast cancer | 137912 |
| Triamcinolone acetonide | Triesence ™ | Glucocorticoid | DME, For treatment of inflammation of the retina | 435 |
| Troglitazone | | Thiazolidinediones | | |
| Tumistatin | | | | |
| Urofollitropin | Fertinex ™ (Serono S.A.) | Fertility Agents | For treatment of female infertility | 78296 |
| Urokinase | Abbokinase ™; Abbokinase ™ (Abbott Laboratories) | Thrombolytic Agents | For the treatment of 67ulmonary embolism, coronary artery thrombosis and IV catheter clearance | 90569 |
| Vandetanib | | Tyrosine Kinase Inhibitors | | 475 |
| Vasopressin | Pitressin ™; Pressyn ™ | Antidiuretics; Oxytocics; Vasoconstrictor Agents | For the treatment of enuresis, polyuria, diabetes insipidus, polydipsia and oesophageal varices with bleeding | 46800 |
| Vatalanib | | Tyrosine Kinase Inhibitors | | 347 |
| VEGF receptor kinase inhibitor | | | | |
| VEGF Trap | Aflibercept ™ (Regneron Pharmaceuticals, Bayer HealthCare AG) | Genetically Engineered Antibodies | DME, cancer, retinal vein occlusion, choroidal neovascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |

TABLE 1-continued

Therapeutic Agent List

| Generic Name | Brands (Companies) | Category | Indication | Molecular Weight |
|---|---|---|---|---|
| Volociximab | Ophthotech | alpha5beta1 Integrin Inhibitor | AMD | |
| XL765 | Exelixis/Sanofi-Aventis | Pl3k/mTOR Inhibition | AMD, DME | |

What is claimed is:

1. A drug delivery device configured to be at least partially implanted in an eye, the device comprising:
   a retention structure positioned near a proximal end region of the device;
   a porous drug release element positioned in fluid communication with an outlet of the device;
   an elongated core element having a longitudinal axis; and
   a reservoir formed of a non-compliant material positioned around the elongated core element, the reservoir having a volume configured to contain one or more therapeutic agents and to be in fluid communication with the outlet through the porous drug release element,
   wherein the device is configured to be at least partially inserted into the eye, and
   wherein the reservoir is configured to enlarge in a non-distensible manner from an insertion configuration having a first three-dimensional shape to a deployed configuration having a second three-dimensional shape, such that the second three-dimensional shape is eccentrically positioned relative to the longitudinal axis of the elongated core element.

2. The device of claim 1, wherein a first portion of the volume of the reservoir in the deployed configuration unfolds away from the lens of the eye and is greater than a remaining portion of the volume.

3. The device of claim 2, wherein the first portion and the remaining portion each remain outside the visual axis of the eye.

4. The device of claim 1, wherein a proximal end of the reservoir is separated a distance from one or more internal tissue surfaces surrounding a penetration site of the eye when in the deployed configuration.

5. The device of claim 1, wherein the elongated core element extends from the proximal end region of the device to a distal end region of the device.

6. The device of claim 5, wherein the drug release element is coupled to the elongated core element near the distal end region of the device and the retention structure is coupled to the elongated core element near the proximal end region of the device.

7. The device of claim 5, wherein the elongated core element comprises an inner lumen and one or more openings extending through a wall of the elongated core element, wherein the inner lumen of the elongated core element is in fluid communication with the reservoir volume through the one or more openings.

8. The device of claim 7, wherein the elongated core element comprises a cylindrical geometry and further comprises a flow director to direct flow through the one more openings.

9. The device of claim 8, wherein the flow director comprises a first cylindrical region coupled to a second cylindrical region by a funnel shaped region, wherein the first cylindrical region has a larger cross-sectional diameter than the second cylindrical region.

10. The device of claim 5, wherein the retention structure comprises a proximal flange element configured to extend outside a sclera of the eye and a neck, the neck having a proximal region configured to extend through a penetration site in the sclera of the eye and a distal extension extending inside the vitreal cavity of the eye.

11. The device of claim 10, wherein the distal extension of the neck surrounds a portion of the elongated core element near the proximal end of the device providing stabilization of the neck to maintain a position of the reservoir.

12. The device of claim 11, wherein the distal extension of the neck prevents contact between the reservoir and internal surfaces of the eye adjacent the penetration site.

13. The device of claim 11, wherein an upper surface of the proximal flange element indicates orientation of the reservoir in the deployed configuration and a direction of eccentricity of the second three-dimensional shape.

14. The device of claim 13, wherein the upper surface indicates orientation due to a shape of the flange element or a mark on the upper surface of the flange element visible to a user from outside the eye.

15. A drug delivery device, the device comprising:
    a proximal end region of the device comprising a retention structure; and
    a distal end region of the device configured to be at least partially implanted into an eye, the distal end region comprising:
       a porous drug release element positioned in fluid communication with an outlet of the device;
       an elongated core element; and
       a reservoir positioned around the elongated core element, the reservoir having a volume configured to contain one or more therapeutic agents and to be in fluid communication with the outlet through the porous drug release element, wherein the reservoir is configured to enlarge from an insertion configuration to a deployed configuration,
    wherein after at least partial implantation in the eye along an axis of insertion, a wall of the reservoir is configured to unfold asymmetrically relative to the elongated core element towards the deployed configuration.

16. The device of claim 15, further comprising a flow director positioned within a lumen of the elongated core element, the flow director configured to facilitate filling of the reservoir volume.

17. The device of claim 16, wherein the flow director comprises a first cylindrical region coupled to a second cylindrical region by a funnel-shaped region to direct flow through one or more openings in the elongated core element, wherein the first cylindrical region has a larger cross-sectional diameter than the second cylindrical region.

18. The device of claim 15, wherein the wall of the reservoir configured to unfold asymmetrically formed a major portion of the reservoir relative to the elongated core element and a minor portion relative to the elongated core element.

19. The device of claim 18, wherein after expansion of the reservoir into the deployed configuration inside the eye, the major portion is directed away from anterior tissue of a vitreal cavity of the eye.

20. The device of claim 15, wherein the retention structure comprises a proximal flange element configured to extend outside a sclera of the eye and a neck, the neck having a proximal region configured to extend through a penetration site in the sclera of the eye and a distal extension extending inside the sclera of the eye.

21. The device of claim 20, wherein the distal extension of the neck surrounds a portion of the elongated core element near the proximal end of the device providing stabilization of the neck to maintain a position of the reservoir.

22. The device of claim 21, wherein the distal extension of the neck prevents contact between the reservoir and internal surfaces of the eye adjacent the penetration site.

* * * * *